United States Patent
Genet et al.

(10) Patent No.: US 6,340,371 B1
(45) Date of Patent: Jan. 22, 2002

(54) CATIONIC ORTHO-PHENYLENEDIAMINES, THEIR USE FOR THE OXIDATION DYEING OF KERATIN FIBERS, DYE COMPOSITIONS AND DYEING PROCESSES

(75) Inventors: Alain Genet, Aulnay sous Bois; Alain Lagrange, Coupvray, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/387,516

(22) Filed: Sep. 1, 1999

(30) Foreign Application Priority Data

Sep. 2, 1998 (FR) .............................. 98 10978

(51) Int. Cl.$^7$ .................. A61K 7/13; C07C 211/00; C07D 233/00
(52) U.S. Cl. .................. 8/406; 8/408; 8/409; 8/416; 8/423; 8/426; 8/655; 564/282; 548/300.1; 548/335.5; 548/346.1; 546/329
(58) Field of Search ................. 8/405, 406, 408, 8/409, 416, 423, 426, 568, 573, 655; 564/282; 548/300.1, 335.5, 346.1; 546/329

(56) References Cited

U.S. PATENT DOCUMENTS

| | | | |
|---|---|---|---|
| 3,622,629 A | * 11/1971 | Lugosy | 564/287 |
| 4,581,370 A | * 4/1986 | Diamond et al. | 548/335.5 |
| 4,888,025 A | * 12/1989 | Bugaut et al. | 8/408 |
| 4,975,092 A | * 12/1990 | Chan et al. | 8/408 |
| 5,139,532 A | 8/1992 | Chan et al. | 8/405 |
| 5,169,403 A | 12/1992 | Chan et al. | 8/405 |
| 5,223,626 A | * 6/1993 | Vincze et al. | 546/329 |

FOREIGN PATENT DOCUMENTS

| | | |
|---|---|---|
| FR | 2 520 358 | 7/1983 |
| FR | 2 586 913 | 3/1987 |
| FR | 2 766 178 | 1/1999 |
| GB | 2 129 022 | 5/1984 |
| WO | WO 99/03819 | 1/1999 |

OTHER PUBLICATIONS

J.F. Corbett, "Recent Developments in the Synthesis of Hair Dyes", Journal of the Society of Dyers and Colourists, vol. 84, Nov. 1968, pp. 556–557.
Ortho Diamino–Benzenes Avec Azote Extra–Nucleaire Quaternise, pp. 9–11, Jan. 1999.
English language Derwent Abstract of FR 2 520 358, Jul. 1983.
English language Derwent Abstract of FR 2 586 913, Mar. 1987.
English language Derwent Abstract of FR 2 766 178, Jan. 1999.

* cited by examiner

*Primary Examiner*—Margaret Einsmann
(74) *Attorney, Agent, or Firm*—Finnegan, Henderson, Farabow, Garrett, and Dunner, L.L.P.

(57) ABSTRACT

Monobenzenic ortho-phenylenediamines comprising at least one cationic group Z, Z being chosen from aliphatic chains, comprising at least one quaternized unsaturated ring, to their use for the oxidation dyeing of keratin fibers, to dye compositions containing them and to oxidation dyeing processes using them.

31 Claims, No Drawings

CATIONIC ORTHO-PHENYLENEDIAMINES, THEIR USE FOR THE OXIDATION DYEING OF KERATIN FIBERS, DYE COMPOSITIONS AND DYEING PROCESSES

The invention relates to monobenzenic ortho-phenylenediamines comprising at least one cationic group Z, to their use for the oxidation dyeing of keratin fibres, to dye compositions containing them, and to oxidation dyeing processes using them. Z is chosen from aliphatic chains containing at least one quaternized unsaturated ring.

It is known practice to dye keratin fibres, and in particular human hair, with dye compositions containing oxidation dye precursors, in particular para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds. The variety of molecules used as oxidation bases and couplers makes it possible to obtain a wide range of colours.

Oxidation dyes, by which so-called "permanent" coloration can be obtained, should have no toxicological drawbacks, should allow shades of the desired strength to be obtained, and should have good resistance to external agents (e.g., light, bad weather, washing, permanent-waving, perspiration and friction).

The dyes should also allow white hairs to be covered, and they should be as unselective as possible, i.e. they should allow the smallest possible differences in coloration to be produced over the entire length of the same keratin fibre, which may indeed be differently sensitized (i.e. damaged) between its tip and its root.

The inventors have discovered, surprisingly and unexpectedly, that a novel family of monobenzenic ortho-phenylenediamines of formula (I), defined below, can be suitable for use as oxidation bases or as couplers or as self-oxidizing compounds for oxidation dyeing, and can also allow dye compositions to be obtained which can lead to strong colorations, in a wide range of shades, and which can have excellent properties of resistance to the various treatments to which keratin fibres may be subjected. These compositions can also be readily synthesized.

The monobenzenic ortho-phenylenediamines of formula (I) comprise at least one cationic group Z, wherein Z is chosen from aliphatic chains containing at least one quaternized unsaturated ring.

These discoveries form the basis of the present invention.

A subject of the invention is thus an ortho-phenylenediamine of formula (I) below, or an acid addition salt thereof:

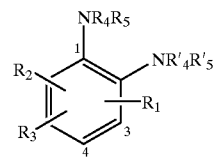

in which:

$R_1$, $R_2$, and $R_3$, which may be identical or different, are radicals chosen from a hydrogen atom; halogens; Z groups; $(C_1-C_6)$alkylcarbonyls; amino$(C_1-C_6)$alkylcarbonyls; N—Z-amino$(C_1-C_6)$alkylcarbonyls; N—$(C_1-C_6)$alkylamino$(C_1-C_6)$alkylcarbonyls; N,N-di$(C_1-C_6)$alkylamino$(C_1-C_6)$alkylcarbonyls; amino$(C_1-C_6)$alkylcarbonyl$(C_1-C_6)$alkyls; N—Z-amino$(C_1-C_6)$alkylcarbonyl$(C_1-C_6)$alkyls; N—$(C_1-C_6)$alkylamino$(C_1-C_6)$alkylcarbonyl$(C_1-C_6)$alkyls; N,N-di$(C_1-C_6)$alkylamino$(C_1-C_6)$alkylcarbonyl$(C_1-C_6)$alkyls; carboxyl; $(C_1-C_6)$alkylcarboxyls; $(C_1-C_6)$alkylsulphonyls; aminosulphonyls; N—Z-aminosulphonyls; $(C_1-C_6)$N-alkylaminosulphonyls; N,N-di$(C_1-C_6)$alkylaminosulphonyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; carbamyl; N—$(C_1-C_6)$alkylcarbamyls; N,N-di$(C_1-C_6)$alkylcarbamyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$alkyls; $(C_1-C_6)$monohydroxyalkyls; $(C_2-C_6)$polyhydroxyalkyls; $(C_1-C_6)$alkoxy$(C_1-C_6)$alkyls; $(C_1-C_6)$trifluoroalkyls; a cyano group; $OR_6$ and $SR_6$ groups; amino groups protected with a radical chosen from $(C_1-C_6)$alkylcarbonyls, $(C_1-C_6)$alkylcarboxyls, trifluoro$(C_1-C_6)$alkylcarbonyls, amino$(C_1-C_6)$alkylcarbonyls, N—Z-amino$(C_1-C_6)$alkylcarbonyls, N—$(C_1-C_6)$alkylamino$(C_1-C_6)$alkylcarbonyls, N,N-di$(C_1-C_6)$alkylamino $(C_1-C_6)$alkylcarbonyls, $(C_1-C_6)$alkylcarboxyls, carbamyl, N—$(C_1-C_6)$alkylcarbamyls, N,N-di$(C_1-C_6)$alkylcarbamyls, $(C_1-C_6)$alkylsulphonyls, aminosulphonyls, N—Z-aminosulphonyls, $(C_1-C_6)$N-alkylaminosulphonyls, N,N-di$(C_1-C_6)$alkylaminosulphonyls, thiocarbamyl radicals, formyl radicals, and Z groups, wherein the linker arm B of the Z groups comprises a ketone function directly attached to the nitrogen atom of the amino group; and $(C_1-C_6)$aminoalkyls in which the amine is substituted with one or two identical or different radicals chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$alkylcarbamyls, $(C_1-C_6)$alkylsulphonyls, formyls, trifluoro$(C_1-C_6)$alkylcarbonyls, $(C_1-C_6)$alkylcarboxyls, thiocarbamyl, and Z groups;

$R_6$ is a radical chosen from $(C_1-C_6)$alkyls; $(C_1-C_6)$monohydroxyalkyls; $(C_2-C_6)$polyhydroxyalkyls; Z groups; $(C_1-C_6)$alkoxy$(C_1-C_6)$alkyl; aryls; benzyl; carboxy$(C_1-C_6)$alkyls; $(C_1-C_6)$alkylcarboxy$(C_1-C_6)$alkyls; cyano$(C_1-C_6)$alkyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$ trifluoroalkyls; $(C_1–C_6)$aminosulphonylalkyls; $(C_1–C_6)$N—Z-aminosulphonylalkyls; N—$(C_1–C_6)$alkylaminosulphonyl$(C_1–C_6)$alkyls; N,N-di$(C_1–C_6)$alkylaminosulphonyl$(C_1–C_6)$alkyls; $(C_1–C_6)$alkylsulphinyl$(C_1–C_6)$alkyls; $(C_1–C_6)$alkylsulphonyl$(C_1–C_6)$alkyls; $(C_1–C_6)$alkylcarbonyl$(C_1–C_6)$alkyls; $(C_1–C_6)$aminoalkyls; $(C_1–C_6)$aminoalkyls in which the amine is substituted with one or two identical or different radicals chosen from $(C_1–C_6)$alkyls, $(C_1–C_6)$monohydroxyalkyls, $(C_2–C_6)$polyhydroxyalkyls, $(C_1–C_6)$alkylcarbonyls, formyls, trifluoro-$(C_1–C_6)$alkylcarbonyls, $(C_1–C_6)$alkylcarboxyls, carbamyl, N—$(C_1–C_6)$alkylcarbamyls, N,N-di-$(C_1–C_6)$alkylcarbamyls, thiocarbamyl, $(C_1–C_6)$alkylsulphonyls, and Z groups;

$R_4$, $R'_4$, $R_5$ and $R'_5$, which may be identical or different, are radicals chosen from a hydrogen atom; Z groups; $(C_1–C_6)$alkyls; $(C_1–C_6)$monohydroxyalkyls; $(C_2–C_6)$polyhydroxyalkyls; $(C_1–C_6)$alkoxy$(C_1–C_6)$alkyls; aryls; benzyl; cyano$(C_1–C_6)$alkyls; carbamyl$(C_1–C_6)$alkyls; N—$(C_1–C_6)$alkylcarbamyl$(C_1–C_6)$alkyls; N,N-di$(C_1–C_6)$alkylcarbamyl$(C_1–C_6)$alkyls; thiocarbamyl$(C_1–C_6)$alkyls; $(C_1–C_6)$trifluoroalkyls; $(C_1–C_6)$sulphoalkyls; $(C_1–C_6)$alkylcarboxy$(C_1–C_6)$alkyls; $(C_1–C_6)$alkylsulphinyl$(C_1–C_6)$alkyls; $(C_1–C_6)$aminosulphonylalkyls; $(C_1–C_6)$N—Z-aminosulphonylalkyls; N—$(C_1–C_6)$alkylaminosulphonyl$(C_1–C_6)$alkyls; N,N-di$(C_1–C_6)$alkylaminosulphonyl$(C_1–C_6)$alkyls; $(C_1–C_6)$alkylcarbonyl$(C_1–C_6)$alkyls; $(C_1–C_6)$aminoalkyls; $(C_1–C_6)$aminoalkyls in which the amine is substituted with one or two identical or different radicals chosen from $(C_1–C_6)$alkyls, $(C_1–C_6)$monohydroxyalkyls, $(C_2–C_6)$polyhydroxyalkyls, $(C_1–C_6)$alkylcarbonyls, carbamyl, N—$(C_1–C_6)$alkylcarbamyls, N,N-di$(C_1–C_6)$alkylcarbamyls, $(C_1–C_6)$alkylsulphonyls, formyl, trifluoro$(C_1–C_6)$alkylcarbonyls, $(C_1–C_6)$alkylcarboxyls, thiocarbamyl, and Z groups;

Z is chosen from unsaturated cationic groups of formulae (II) and (III) below, and the saturated cationic groups of formula (IV) below:

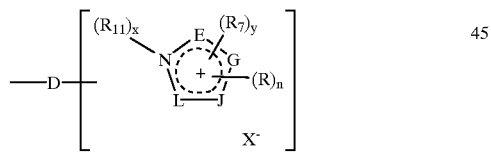

(II)

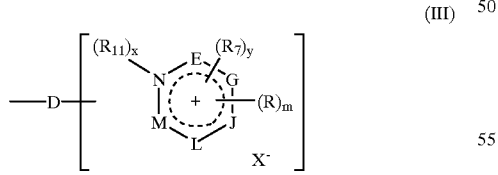

(III)

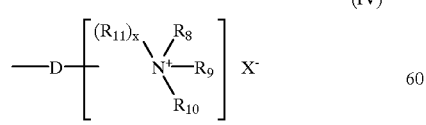

(IV)

in which:
D is a linker arm chosen from linear and branched alkyl chains, optionally interrupted by at least one hetero atom, such as oxygen, sulphur, and nitrogen atoms, and optionally substituted with at least one radical chosen from a hydroxyl group and $(C_1–C_6)$alkoxys, and which can optionally bear at least one ketone function; in an embodiment of the invention, the alkyl chains comprise from 1 to 14 carbon atoms;

the ring members E, G, J, L and M, which may be identical or different, are chosen from carbon, oxygen, sulphur, and nitrogen atoms;

n is chosen from the integers 0, 1, 2, 3, and 4;

m is chosen from the integers 0, 1, 2, 3, 4, and 5;

the radicals R, which may be identical or different, are chosen from a second group Z which is identical to or different from the first group Z, a halogen atom, a hydroxyl, $(C_1–C_6)$alkyls, $(C_1–C_6)$monohydroxyalkyls, $(C_2–C_6)$polyhydroxyalkyls, a nitro, a cyano, cyano$(C_1–C_6)$alkyls, $(C_1–C_6)$alkoxys, tri$(C_1–C_6)$alkylsilane$(C_1–C_6)$alkyls, amido, aldehydo, carboxyl, $(C_1–C_6)$alkylcarbonyls, thio, $(C_1–C_6)$thioalkyls, $(C_1–C_6)$alkylthios, amino, aminos protected with a radical chosen from $(C_1–C_6)$alkylcarbonyls, carbamyls and $(C_1–C_6)$alkylsulphonyls; NHR" groups, NR"R'" groups in which R" and R'", which may be identical or different, are chosen from $(C_1–C_6)$alkyl radicals, $(C_1–C_6)$monohydroxyalkyl radicals, and $(C_2–C_6)$polyhydroxyalkyl radicals;

$R_7$ is a radical chosen from $(C_1–C_6)$alkyls, $(C_1–C_6)$monohydroxyalkyls, $(C_2–C_6)$polyhydroxyalkyls, cyano$(C_1–C_6)$alkyls, tri$(C_1–C_6)$alkylsilane$(C_1–C_6)$alkyls, $(C_1–C_6)$alkoxy$(C_1–C_6)$alkyls, carbamyl-$(C_1–C_6)$alkyls, $(C_1–C_6)$alkylcarboxy$(C_1–C_6)$alkyls, benzyl and a second group Z which is identical to or different from the first group Z;

$R_8$, $R_9$ and $R_{10}$, which may be identical or different, are radicals chosen from $(C_1–C_6)$alkyls, $(C_1–C_6)$monohydroxyalkyls, $(C_2–C_6)$polyhydroxyalkyls, $(C_1–C_6)$alkoxy$(C_1–C_6)$alkyls, cyano$(C_1–C_6)$alkyls, aryls, benzyl, $(C_1–C_6)$amidoalkyls, tri$(C_1–C_6)$alkylsilane$(C_1–C_6)$alkyls, and $(C_1–C_6)$aminoalkyls in which the amine is protected with a radical chosen from $(C_1–C_6)$alkylcarbonyls, carbamyl, and $(C_1–C_6)$alkylsulphonyls; two of the radicals $R_8$, $R_9$ and $R_{10}$ can together also form, with the nitrogen atom to which they are attached, a saturated 5- or 6-membered ring or a ring containing at least one additional hetero atom such as, for example, a pyrrolidine ring, a piperidine ring, a piperazine ring or a morpholine ring, the ring being optionally substituted with a substituent chosen from halogen atoms, a hydroxyl group, $(C_1–C_6)$alkyls, $(C_1–C_6)$monohydroxyalkyls, $(C_2–C_6)$polyhydroxyalkyls, a nitro, a cyano, cyano$(C_1–C_6)$alkyls, $(C_1–C_6)$alkoxys, tri$(C_1–C_6)$alkylsilane$(C_1–C_6)$alkyls, amido, aldehydo, carboxyl, keto$(C_1–C_6)$alkyls, thio, $(C_1–C_6)$thioalkyls, $(C_1–C_6)$alkylthios, amino, and aminos protected with a radical chosen from $(C_1–C_6)$alkylcarbonyls, carbamyl, and $(C_1–C_6)$alkylsulphonyls; one of the radicals $R_8$, $R_9$ and $R_{10}$ can also be chosen from a second group Z which is identical to or different from the first group Z;

$R_{11}$ is a radical chosen from $(C_1–C_6)$alkyls; $(C_1–C_6)$monohydroxyalkyls; $(C_2–C_6)$polyhydroxyalkyls; aryls; benzyl; $(C_1–C_6)$aminoalkyls, $(C_1–C_6)$aminoalkyls in which the amine is protected with a radical chosen from $(C_1–C_6)$alkylcarbonyls, carbamyl, and $(C_1–C_6)$alkylsulphonyls; carboxy$(C_1–C_6)$alkyls; cyano$(C_1–C_6)$alkyls; carbamyl $(C_1-C_6)$alkyls; $(C_1-C_6)$trifluoroalkyls; tri$(C_1-C_6)$alkylsilane$(C_1-C_6)$alkyls; $(C_1-C_6)$sulphonamidoalkyls; $(C_1-C_6)$alkylcarboxy$(C_1-C_6)$alkyls; $(C_1-C_6)$alkylsulphinyl$(C_1-C_6)$alkyls; $(C_1-C_6)$alkylsulphonyl$(C_1-C_6)$alkyls; $(C_1-C_6)$alkylketo$(C_1-C_6)$alkyls; N—$(C_1-C_6)$alkylcarbamyl$(C_1-C_6)$alkyls; N—$(C_1-C_6)$alkylsulphonamido$(C_1-C_6)$alkyls;

x and y are integers chosen from 0 and 1; with the provision that:

in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical $R_7$ is borne by the nitrogen atom of the unsaturated ring; or alternatively
2) when at least one of the ring members E, G, J and L represents a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is chosen from divalent atoms and when the radical $R_7$ is borne by the nitrogen atom of the unsaturated ring;

in the cationic groups of formula (IV):
when x=0, then the linker arm is attached to the nitrogen atom bearing the radicals $R_8$ to $R_{10}$,
when x=1, then two of the radicals $R_8$ to $R_{10}$ form, together with the nitrogen atom to which they are attached, a saturated 5- or 6-membered ring as defined above, and the linker arm D is borne by a carbon atom of the saturated ring;

$X^-$ is chosen from monovalent and divalent anions, in an embodiment of the invention, $X^-$ is chosen from halogen atoms such as chlorine, bromine, fluorine, and iodine, a hydroxide, a hydrogenosulphate, and $(C_1-C_6)$alkyl sulphates such as, for example, a methyl sulphate or an ethyl sulphate;

it being understood that:
the number of unsaturated cationic groups Z of formula (II) or (III) is at least equal to 1;
when at least one of $R_4$, $R_5$, $R'_4$, and $R'_5$ is chosen from Z groups in which the linker arm D represents an alkyl chain comprising a ketone function, then the ketone function is not directly attached to the nitrogen atom of the group —$NR_4R_5$ or —$NR'_4R'_5$.

As mentioned above, these ortho-phenylenediamines of formula (I) are compounds which can be used for the oxidation dyeing of keratin fibres and can have the advantage of behaving both like an oxidation base and like a coupler, or like self-oxidizing compounds, i.e. compounds capable of dyeing keratin fibres without using any oxidizing agent other than atmospheric oxygen. The oxidation dye compositions containing those novel ortho-phenylenediamines of formula (I) in accordance with the invention can lead to intense colorations with a very wide variety of shades. The colorations obtained using these ortho-phenylenediamines of formula (I) moreover can have excellent properties of resistance with respect to the action of various external agents (e.g., light, bad weather, washing, permanent waving, perspiration, friction).

In formula (I) above, the alkyl and alkoxy radicals can be linear or branched.

Representative rings of the unsaturated groups Z of formula (II) above, include, for example, pyrrole, imidazole, pyrazole, oxazole, thiazole and triazole rings.

Representative rings of the unsaturated groups Z of formula (III) above, include, for example, pyridine, pyrimidine, pyrazine, oxazine and triazine rings.

Compounds of formula (I) above, include:
3-[3-(2-aminophenylamino)propyl]-1-methyl-3H-imidazol-1-ium monochloride;
3-[2-(2-aminophenylamino)ethyl]-1-methyl-3H-imidazol-1-ium monochloride;
4-[2-(1-methyl-3H-imidazol-1-ium)ethoxy]-$N_2$-[2-(1-methyl-3H-imidazol-1-ium)ethyl]benzene-1,2-diamine dichloride;
3-[2-(2-amino-4-methylphenylamino)ethyl]-1-ethyl-3H-imidazol-1-ium monochloride;
3-[3-(2-aminophenylamino)propyl]-1-(3-trimethylammonium-2-hydroxypropyl)-3H-imidazol-1-ium dichloride;
3-[3-(2-aminophenylamino)propyl]-1-(2-hydroxyethyl)-3H-imidazol-1-ium monobromide;
3-{[2-(2-aminophenylamino)ethylcarbamoyl]methyl}-1-methyl-3H-imidazol-1-ium monochloride;
1-[2-(2-amino-4-chlorophenylamino)ethyl]pyridinium monochloride;
3-[2-(2-amino-5-methoxyphenylamino)ethyl]-1-methyl-3H-imidazol-1-ium monochloride;
3-[2-(2-amino-5-methylsulphanylphenylamino)ethyl]-1-methyl-3H-imidazol-1-ium monochloride;
and the acid addition salts thereof.

Compounds of formula (I) in accordance with the invention can be obtained by known methods, for example by reduction of the corresponding cationic nitro compounds (cationic ortho-nitroanilines).

This reduction step (production of a primary aromatic amine), which may or may not be followed by a salification, is generally, for convenience, the final step of the synthesis.

This reduction can take place earlier in the sequence of reactions leading to the preparation of the compounds of formula (I), however, the primary amine created (for example by an acetylation, benzenesulphonation, etc. step) should then be "protected", for example, by known methods before carrying out the desired substitution(s) or modification(s) (including quaternization) and in the end the amine function may be "deprotected" (generally in acidic medium).

When the synthesis is complete, the compounds of formula (I) in accordance with the invention can, if necessary, be recovered by methods which are well known in the state of the art, such as crystallization or distillation.

Another subject of the invention is the use of the compounds of formula (I) and acid addition salts thereof in accordance with the invention as oxidation bases, coupling bases, or even as self-oxidizing dyes for the oxidation dyeing of keratin fibres, and in of particular human keratin fibres such as the hair.

The compounds of formula (I) and acid addition salts thereof in accordance with an embodiment of the invention are used as couplers for the oxidation dyeing of keratin fibres.

The invention also relates to a composition for the oxidation dyeing of keratin fibres, and in particular of human keratin fibres such as the hair, comprising, in a medium which is suitable for dyeing, at least ingredient chosen from compounds of formula (I) and acid addition salts thereof in accordance with the invention.

The at least one ingredient is present in the dye composition, in an embodiment of the invention, in an amount generally ranging from 0.0005 to 12% by weight relative to the total weight of the dye composition, particularly the amount ranges from 0.005 to 6% by weight relative to this weight.

According to a preferred embodiment of the invention, the dye composition also includes one or more oxidation bases which can be chosen from the oxidation bases conventionally used in oxidation dyeing, including para-phenylenediamines, bis(phenylo)alkylenediamines, para-aminophenols, ortho-aminophenols, and heterocyclic bases.

Para-phenylenediamines include, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

In particular, the para-phenylenediamines mentioned above, include para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Bis(phenyl)alkylenediamines include, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Para-aminophenols include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Ortho-aminophenols include, for example, 2-aminophenol, 2-amino-5-methylphenol, 2-amino-6-methylphenol and 5-acetamido-2-aminophenol, and the acid addition salts thereof.

Heterocyclic bases include, for example, pyridine derivatives, pyrimidine derivatives and pyrazole derivatives.

When they are used, these oxidation bases are present, in an embodiment of the invention, in an amount generally ranging from 0.0005 to 12% by weight relative to the total weight of the dye composition, particularly the amount ranges from 0.005 to 6% by weight relative to this weight.

In addition to the compound(s) of formula (I) above, the dye composition in accordance with the invention can also include one or more couplers which can be chosen from the couplers used conventionally in oxidation dyeing, including meta-phenylenediamines, meta-aminophenols, meta-diphenols and heterocyclic couplers such as, for example, indole derivatives, indolene derivatives, pyridine derivatives and pyrazolones, and the acid addition salts thereof.

More specific examples of these couplers, include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the acid addition salts thereof.

When they are present, these couplers are present in the dye composition, in one embodiment, in amount generally ranging from 0.0001 to 10% by weight relative to the total weight of the dye composition, particularly the amount ranges from 0.005 to 5% by weight approximately relative to this weight.

In general, the addition salts with an acid which can be used in the context of the invention (compounds of formula (I), oxidation bases and couplers) are chosen from hydrochlorides, hydrobromides, sulphates, citrates, succinates, tartrates, lactates, and acetates.

The medium suitable for dyeing (or the support) can be chosen from water and a mixture of water and at least one organic solvent to dissolve the compounds which would not be sufficiently soluble in water. Suitable organic solvents, include, for example, ($C_1$–$C_4$) lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol and phenoxyethanol, similar products and mixtures thereof.

In an embodiment of the invention, the solvents can be present in an amount generally ranging from 1 and 40% by weight relative to the total weight of the dye composition, particularly in an amount ranging from 5 to 30% by weight.

The pH of the dye composition in accordance with an embodiment of the invention generally ranges from 3 to 12 particularly from 5 to 11. The pH can be adjusted to the desired value using acidifying or basifying agents commonly used to dye keratin fibres.

Acidifying agents include, for example, inorganic and organic acids such as hydrochloric acid, orthophosphoric acid, sulphuric acid, carboxylic acids such as acetic acid, tartaric acid, citric acid and lactic acid, and sulphonic acids.

Basifying agents include, for example, aqueous ammonia, alkaline carbonates, alkanolamines such as mono-, di- and triethanolamine and derivatives thereof, sodium hydroxide, potassium hydroxide and the compounds of formula (V) below:

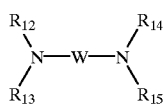
(V)

in which W is chosen from propylene residues optionally substituted with a substituent chosen from a hydroxyl group and($C_1$–$C_6$)alkyls; $R_{12}$, $R_{13}$, $R_{14}$ and $R_{15}$, which may be identical or different, are radicals chosen from a hydrogen atom, ($C_1$–$C_6$)alkyls, and ($C_1$–$C_6$)hydroxyalkyls.

The oxidation dye compositions in accordance with the invention can also include at least one direct dye, in particular to modify the shades or to enrich them with glints. The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above. According to this process, at least one dye composition as defined above is applied to the fibres for a period which is sufficient to develop the desired coloration, either in air or using an oxidizing agent. The dye composition can optionally contain oxidation catalysts, in order to accelerate the oxidation process.

According to an embodiment of the process of the invention, the coloration of the fibres can be carried out without addition of an oxidizing agent, merely by contact with atmospheric oxygen, i.e., the air.

According to another embodiment of the process of the invention, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially in a separate manner. According to this embodiment of the dyeing process of the invention, the dye composition described above can be mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for a period of time sufficient to develop the desired coloration afterwhich the fibres are rinsed, washed with shampoo, rinsed again and dried. In an embodiment of the invention, the period of time generally ranges from 3 to 50 minutes, and can be 5 to 30 minutes.

The oxidizing agent present in the oxidizing composition and as defined above can be chosen from the oxidizing agents conventionally used for the oxidation dyeing of keratin fibres, including hydrogen peroxide, urea peroxide, alkali metal bromates and persalts such as perborates and persulphates, and enzymes such as peroxidases and 2-electron oxidoreductases. In an embodiment of the invention, the oxidating agent is hydrogen peroxide.

In one embodiment of the invention, the pH of the oxidizing composition containing the oxidizing agent as defined above is such that, after mixing with the dye composition, the pH of the resultant composition applied to the keratin fibres generally range from 3 to 12, and particularly from 5 to 11. The pH is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, comprising a first compartment of which contains the dye composition as defined above and a second compartment of which contains the oxidizing composition as defined above. These devices can be equipped with a means for delivering the desired mixture onto the hair, such as the devices described in patent FR 2,586,913, the disclosure of which is herein specifically incorporated by reference.

The examples which follow are intended to illustrate the invention without, however, limiting its scope.

PREPARATION EXAMPLE

PREPARATION OF 3-[3-(2-AMINOPHENYLAMINO)PROPYL]-1-METHYL-3H-IMIDAZOL-1-IUM MONOCHLORIDE HYDROCHLORIDE

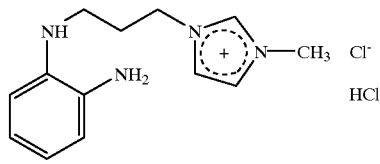

a) Synthesis of (3-imidazol-1-ylpropyl)(2-nitrophenyl)amine

A mixture of 187.8 g (1.5 mol) of 3-imidazol-1-ylpropylamine and 82.8 g (0.6 mol) of potassium carbonate in 280 ml of water was heated on a boiling water bath.

141.1 g (1 mol) of 1-fluoro-2-nitrobenzene was added dropwise over 50 minutes and maintained at a temperature of 90–95° C. for 2 hours.

The mixture was cooled in a bath of ice and the crystallized precipitate was filtered off, washed with water and recrystalized from refluxing isopropanol. 109.3 g of orange-yellow crystals melting at 80° C. (Kofler) were obtained, the elemental analysis for which product, calculated for $C_{12}H_{14}N_4O_2$, was:

| % | C | H | N | O |
|---|---|---|---|---|
| Calculated | 58.53 | 5.73 | 22.75 | 12.99 |
| Found | 58.40 | 5.78 | 22.54 | 13.07 | b) Quaternization of (3-imidazol-1-ylpropyl)(2-nitrophenyl)amine

A suspension of 61.5 g (0.25 mol) of (3-imidazo)-1-ylpropyl)(2-nitrophenyl)amine, prepared above in the preceding step, and 26.0 ml (0.27 mol) of dimethyl sulphate in 800 ml of ethyl acetate was prepared and stirred for 3 hours at 50° C.

The oily precipitate was separated out after settling of the phases, washed several times with ethyl acetate and dried at 40° C. under vacuum.

81.3 g of a yellow oil were obtained, the elemental analysis of which product, calculated for $C_{14}H_{20}N_4O_6S \cdot 0.5H_2O$ was:

| % | C | H | N | O | S |
|---|---|---|---|---|---|
| Calculated | 44.09 | 5.55 | 14.69 | 27.22 | 8.41 |
| Found | 44.80 | 5.56 | 14.55 | 27.23 | 8.29 | c) Reduction 75.0 g (0.196 mol) of the compound obtained above in the previous step, 12 g of 5% palladium-on-charcoal (containing 50% water), 300 ml of 96° ethanol and 300 ml of water were placed in a hydrogenator.

The reduction took place in half an hour under a hydrogen pressure of about 8 bar and at a temperature which was gradually raised to 75° C.

After filtering off the catalyst under nitrogen, the filtrate was poured into 100 ml of 36% hydrochloric acid and evaporated to dryness under reduced pressure.

The compound was taken up several times in approximately 5N absolute hydrochloric ethanol. After recrystallization from a refluxing ethanol/water mixture and drying at 40° C. under vacuum and over potassium hydroxide, 23.0 g of slightly violet crystals of 3-[3-(2-aminophenylamino)propyl]-1-methyl-3H-imidazol-1-ium monochloride hydrochloride melting with decomposition at 202–204° C. (Kofler) were obtained, the elemental analysis of which product, calculated for $C_{13}H_{20}N_4Cl_2$, was:

| % | C | H | N | Cl |
|---|---|---|---|---|
| Calculated | 51.49 | 6.65 | 18.48 | 23.38 |
| Found | 51.22 | 6.71 | 18.37 | 23.29 |

APPLICATION EXAMPLES

Examples 1 to 4 of Dyeing in Alkaline Medium

The dye compositions below in accordance with the invention were prepared (contents in grams):

| EXAMPLE | 1 | 2 | 3 | 4 |
|---|---|---|---|---|
| 3-[3-(2-Aminophenylamino)-propyl]-1-methyl-3H-imidazol-1-ium monochloride hydrochloride (compound of formula (I)) | 0.909 | 0.909 | 0.909 | 0.909 |
| 4,5-Diamino-1-ethyl-3-methylpyrazole dihydro-chloride (oxidation base) | 0.639 | — | — | — |
| meta-Aminophenol (coupler) | — | 0.327 | — | — |
| 2,4-Diaminophenoxyethanol dihydrochloride (coupler) | — | — | 0.723 | — |
| Common dye support No. 1 | (*) | (*) | (*) | (*) |
| Demineralized water qs | 100 g | 100 g | 100 g | 100 g |

(*) Common dye support No. 1:

| 96° Ethanol | 18 g |
|---|---|
| Sodium metabisulphate as an aqueous 35% solution | 0.68 g |
| Pentasodium salt of diethylenetriamine-pentaacetic acid | 1.1 g |
| 20% aqueous ammonia | 10.0 g |

At the time of use, each of the above dye compositions was mixed, weight for weight, with a 20-volumes hydrogen peroxide solution (6% by weight) of pH 3.

The mixture obtained was applied to locks of permanent-waved grey hair containing 90% white hairs, for 30 minutes. The locks were then rinsed, washed with a standard shampoo, rinsed again and then dried.

The shades obtained are given in the table below:

| EXAMPLE | dyeing pH | shade obtained |
|---|---|---|
| 1 | 10 ± 0.2 | matt golden blonde |
| 2 | 10 ± 0.2 | matt blonde |
| 3 | 10 ± 0.2 | dull green |
| 4 | 10 ± 0.2 | coppery golden blonde |

Examples 5 to 8 of Dyeing in Neutral Medium

The dye compositions below in accordance with the invention were prepared (contents in grams):

| EXAMPLE | 5 | 6 | 7 | 8 |
|---|---|---|---|---|
| 3-[3-(2-Aminophenylamino)-propyl]-1-methyl-3H-imidazol-1-ium monochloride hydrochloride (compound of formula (I)) | 0.909 | 0.909 | 0.909 | 0.909 |
| para-Tolylenediamine dihydrochloride (oxidation base) | 0.585 | — | — | — |
| 1,3-Dihydroxybenzene (coupler) | — | 0.33 | — | — |
| 3,7-Diaminopyrazolopyrimidine dihydrochloride (oxidation base) | — | — | 0.666 | — |
| 4-Hydroxyindole (coupler) | — | — | — | 0.399 |
| Common dye support No. 2 | () | () | () | () |
| Demineralized water qs | 100 g | 100 g | 100 g | 100 g |

(**) Common dye support No. 2:

| 96° Ethanol | 18 g |
|---|---|
| $K_2HPO_4/KH_2PO_4$ (1.5M/1M) buffer | 10 g |
| Sodium metabisulphite | 0.68 g |
| Pentasodium salt of diethylenetriamine-pentaacetic acid | 1.1 g |

At the time of use, each of the above dye compositions was mixed, weight for weight, with a 20-volumes hydrogen peroxide solution (6% by weight) of pH 3.

The mixture obtained was applied to locks of permanent-waved grey hair containing 90% white hairs, for 30 minutes. The locks were then rinsed, washed with a standard shampoo, rinsed again and then dried.

The shades obtained are given in the table below:

| EXAMPLE | dyeing pH | shade obtained |
|---|---|---|
| 5 | 5.7 ± 0.2 | matt ash dark chestnut |
| 6 | 5.7 ± 0.2 | coppery golden light blonde |
| 7 | 5.7 ± 0.2 | deep green |
| 8 | 5.7 ± 0.2 | golden light blonde |

Examples 9 to 12 of Dyeing in Alkaline Medium

The dye compositions below in accordance with the invention were prepared (contents in grams):

| EXAMPLE | 9 | 10 | 11 | 12 |
|---|---|---|---|---|
| 3-[3-(2-Aminophenylamino)propyl]-1-methyl-3H-imidazol-1-ium monochloride hydrochloride (compound of formula (I)) | 0.909 | 0.909 | 0.909 | 0.909 |
| 3,7-Diaminopyrazolopyrimidine dihydrochloride (oxidation base) | 0.666 | — | — | — |
| 1,3-Dihydroxybenzene (coupler) | — | 0.33 | — | — |
| 4-Hydroxyindole (coupler) | — | — | 0.399 | — |
| para-Tolylenediamine dihydrochloride (oxidation base) | — | — | — | 0.585 |
| Common dye support No. 1 | (*) | (*) | (*) | (*) |
| Demineralized water qs | 100 g | 100 g | 100 g | 100 g |

(*) Common dye support No. 1:

This is identical to the one used for Examples 1 to 4 above.

(*) Common Dye Support No. 1:

This is identical to the one used for Examples 1 to 4 above.

At the time of use, each of the above dye compositions was mixed, weight for weight, with an aqueous solution containing $6 \times 10^{-3}$ mol % of ammonium persulphate.

The mixture obtained was applied to locks of permanent-wave grey hair containing 90% white hairs, for 30 minutes. The locks were then rinsed, washed with a standard shampoo, rinsed again and then dried.

The shades obtained are given in the table below:

| EXAMPLE | dyeing pH | shade obtained |
|---|---|---|
| 9 | 10 ± 0.2 | Iridescent mahogany |
| 10 | 10 ± 0.2 | Ash natural blonde |
| 11 | 10 ± 0.2 | Ash natural light blonde |
| 12 | 10 ± 0.2 | Matt ash natural light chestnut |

Examples 13 to 16 of Dyeing in Neutral Medium

The dye compositions below in accordance with the invention were prepared (contents in grams):

| EXAMPLE | 13 | 14 | 15 | 16 |
|---|---|---|---|---|
| 3-[3-(2-Aminophenylamino)propyl]-1-methyl-3H-imidazol-1-ium monochloride hydrochloride (compound of formula (I)) | 0.909 | 0.909 | 0.909 | 0.909 |
| meta-Aminophenol (coupler) | 0.327 | — | — | — |
| 4,5-Diamino-1-ethyl-3-methylpyrazole dihydrochloride (oxidation base) | — | 0.639 | — | — |
| 2,4-Diaminophenoxyethanol dihydrochloride (coupler) | — | — | — | 0.723 |
| Common dye support No. 2 | () | () | () | () |
| Demineralized water qs | 100 g | 100 g | 100 g | 100 g |

(**) Common by support No. 2:

This is identical to the one used for Examples 5 to 8 above.

At the time of use, each of the above dye compositions was mixed, weight for weight, with an aqueous solution containing $6 \times 10^{-3}$ mol % of ammonium persulphate.

The mixture obtained was applied to locks of permanent-wave grey hair containing 90% white hairs, for 30 minutes. The locks were then rinsed, washed with a standard shampoo, rinsed again and then dried.

The shades obtained are given in the table below:

| EXAMPLE | dyeing pH | shade obtained |
|---|---|---|
| 13 | 5.7 ± 0.2 | Matt ash blonde |
| 14 | 5.7 ± 0.2 | Coppery golden blonde |
| 15 | 5.7 ± 0.2 | Golden coppery dark blonde |
| 16 | 5.7 ± 0.2 | Mahogany golden blonde |

Example 17 of Dyeing in Air

At the time of use, the dye composition below in accordance with the invention was prepared:

| | |
|---|---|
| 3-[3-(2-aminophenylamino)propyl]-1-methyl-3H-imidazol-1-ium monochloride hydrochloride (compound of formula (I)) | 1.818 g |
| 96° Ethanol | 20 g |
| pH 9.5 NH$_4$OH/NH$_4$Cl (1M/1M) buffer | 10 g |
| Demineralized water qs | 100 g |

This composition was applied to locks of permanent-waved grey hair containing 90% white hair, and the coloration was allowed to develop for 30 minutes, without addition of any oxidizing agent other than atmospheric oxygen.

The hair was then rinsed, washed with a standard shampoo, rinsed again and then dried.

The hair was dyed in a golden copper shade.

What is claimed is:

1. A compound of formula (1) below or an acid addition salt thereof:

$$\underset{\substack{R_3 \\ 4}}{\overset{\substack{NR_4R_5 \\ 1}}{\underset{3}{\bigcirc}}} \begin{array}{c} NR'_4R'_5 \\ R_1 \end{array} \quad (I)$$

wherein:

$R^1$, $R^2$ and $R^3$, which may be identical or different, are chosen from a hydrogen atom; halogen atoms; Z groups; $(C_1-C_6)$alkylcarbonyls; amino$(C_1-C_6)$alkylcarbonyls; N—Z-amino$(C_1-C_6)$alkylcarbonyls; N—$(C_1-C_6)$alkylamino$(C_1-C_6)$alkyl-carbonyls; N,N-di$(C_1-C_6)$alkylamino$(C_1-C_6)$alkylcarbonyls; amino$(C_1-C_6)$alkylcarbonyl$(C_1-C_6)$alkyls; N—Z-amino$(C_1-C_6)$alkylcarbonyl-$(C_1-C_6)$alkyls; N—$(C_1-C_6)$alkylamino$(C_1-C_6)$alkylcarbonyl$(C_1-C_6)$alkyls; N,N-di$(C_1-C_6)$alkylamino$(C_1-C_6)$alkylcarbonyl$(C_1-C_6)$alkyls; carboxyl; $(C_1-C_6)$alkylcarboxyls; $(C_1-C_6)$alkylsulphonyls; aminosulphonyls; N—Z-aminosulphonyls; $(C_1-C_6)$N-alkylaminosulphonyls; N,N-di$(C_1-C_6)$alkylaminosulphonyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; carbamyl; N—$(C_1-C_6)$alkyl-carbamyls; N,N-di$(C_1-C_6)$alkylcarbamyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$alkyls; $(C_1-C_6)$monohydroxyalkyls; $(C_2-C_6)$polyhydroxyalkyls; $(C_1-C_6)$alkoxy$(C_1-C_6)$-alkyls; $(C_1-C_6)$trifluoroalkyls; cyano; $OR_6$ and $SR_6$ groups; amino groups protected with a radical chosen from $(C_1-C_6)$alkylcarbonyls, $(C_1-C_6)$alkylcarboxyls, trifluoro$(C_1-C_6)$alkylcarbonyls, amino$(C_1-C_6)$alkylcarbonyls, N—Z-amino$(C_1-C_6)$alkylcarbonyls, N—$(C_1-C_6)$alkylamino$(C_1-C_6)$alkylcarbonyls, N,N-di$(C_1-C_6)$alkylamino$(C_1-C_6)$alkylcarbonyls, $(C_1-C_6)$alkylcarboxyls, carbamyl, N—$(C_1-C_6)$alkylcarbamyls, N,N-di$(C_1-C_6)$alkylcarbamyls, $(C_1-C_6)$alkylsulphonyls, aminosulphonyls, N—Z-aminosulphonyls, $(C_1-C_6)$N-alkylaminosulphonyls, N,N-di$(C_1-C_6)$alkylaminosulphonyls, thiocarbamyl, formyl, and Z groups, in which the linker arm D of the Z group comprises a ketone function directly attached to the nitrogen atom of the amino group; and $(C_1-C_6)$aminoalkyl in which the amine is substituted with at least one, identical or different radical, chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkyl-carbamyls, N,N-di$(C_1-C_6)$alkylcarbamyls, $(C_1-C_6)$alkylsulphonyls, formyl, trifluoro $(C_1-C_6)$alkyl-carbonyls, $(C_1-C_6)$alkylcarboxyls, thiocarbamyl, and Z groups;

$R_6$ is a radical chosen from $(C_1-C_6)$alkyls; $(C_1-C_6)$monohydroxyalkyls; $(C_2-C_6)$polyhydroxyalkyls; Z groups; $(C_1-C_6)$alkoxy$(C_1-C_6)$alkyls; aryls; benzyl; carboxy$(C_1-C_6)$alkyls; $(C_1-C_6)$alkylcarboxy$(C_1-C_6)$alkyls; cyano$(C_1-C_6)$alkyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$trifluoroalkyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; $(C_1-C_6)$alkylsulphinyl$(C_1-C_6)$alkyls; $(C_1-C_6)$alkylsulphonyl$(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, formyl, trifluoro-$(C_1-C_6)$alkylcarbonyls, $(C_1-C_6)$alkylcarboxyls, carbamyl, N—$(C_1-C_6)$alkylcarbamyls, N,N-di-$(C_1-C_6)$alkylcarbamyls, thiocarbamyl and $(C_1-C_6)$alkylsulphonyls, and Z groups;

$R_4$, $R'_4$, $R_5$ and $R'_5$, which may be identical or different, are substituents chosen from a hydrogen atom; Z groups; $(C_1-C_6)$alkyls; $(C_1-C_6)$monohydroxyalkyls; $(C_2-C_6)$polyhydroxyalkyls; $(C_1-C_6)$alkoxy$(C_1-C_6)$alkyls; aryls; benzyl; cyano$(C_1-C_6)$alkyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; thiocarbamyl$(C_1-C_6)$alkyls; $(C_1-C_6)$trifluoroalkyls; $(C_1-C_6)$sulphoalkyls; $(C_1-C_6)$alkylcarboxy$(C_1-C_6)$alkyls; $(C_1-C_6)$alkylsulphinyl$(C_1-C_6)$alkyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$alkylcarbamyls, $(C_1-C_6)$alkylsulphonyls, formyl, trifluoro$(C_1-C_6)$alkylcarbonyls, $(C_1-C_6)$alkylcarboxyls, thiocarbamyl, and Z groups;

Z is chosen from unsaturated cationic groups of formulae (II) and (III) below, and the saturated cationic groups of formula (IV) below:

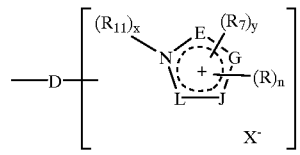

(II)

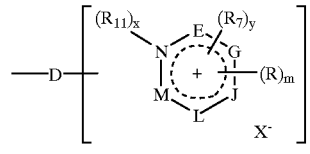

(III)

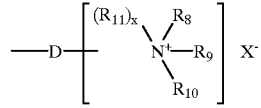

(IV)

in which:

D is a linker arm chosen from linear and branched alkyl chains, optionally interrupted by at least one hetero atom, such as oxygen, sulphur, and nitrogen atoms, and optionally substituted with at least one radical chosen from a hydroxyl group and $(C_1-C_6)$alkoxys, and which can optionally bear at least one ketone function;

the ring members E, G, J, L and M, which may be identical or different, are chosen from carbon, oxygen, sulphur, and nitrogen atoms;

n is chosen from the integers 0, 1, 2, 3, and 4;

m is chosen from the integers 0, 1, 2, 3, 4, and 5;

the radicals R, which may be identical or different, are chosen from a second group Z which is identical to or different from the first group Z, a halogen atom, a hydroxyl, $(C_1-C_6)$alkyls, $(C_1-C_6)$monohydroxyalkyls, $(C_2-C_6)$polyhydroxyalkyls, a nitro, a cyano, cyano$(C_1-C_6)$alkyls, $(C_1-C_6)$ alkoxys, tri($C_1$–$C_6$)alkylsilane($C_1$–$C_6$)alkyls, amido, aldehydo, carboxyl, ($C_1$–$C_6$)alkylcarbonyls, thio, ($C_1$–$C_6$)thioalkyls, ($C_1$–$C_6$)alkylthios, amino, aminos protected with a radical chosen from ($C_1$–$C_6$) alkylcarbonyls, carbamyls and ($C_1$–$C_6$) alkylsulphonyls; NHR'' groups, NR''R''' groups in which R'' and R''', which may be identical or different, are chosen from ($C_1$–$C_6$)alkyl radicals, ($C_1$–$C_6$)monohydroxyalkyl radicals, and ($C_2$–$C_6$)polyhydroxyalkyl radicals;

$R_7$ is a radical chosen from ($C_1$–$C_6$)alkyls, ($C_1$–$C_6$)monohydroxyalkyls, ($C_2$–$C_6$)polyhydroxyalkyls, cyano($C_1$–$C_6$)alkyls, tri($C_1$–$C_6$)alkylsilane($C_1$–$C_6$)alkyls, ($C_1$–$C_6$)alkoxy($C_1$–$C_6$)alkyls, carbamyl-($C_1$–$C_6$)alkyls, ($C_1$–$C_6$)alkylcarboxy($C_1$–$C_6$)alkyls, benzyl and a second group Z which is identical to or different from the first group Z;

$R_8$, $R_9$ and $R_{10}$, which may be identical or different, are radicals chosen from ($C_1$–$C_6$)alkyls, ($C_1$–$C_6$)monohydroxyalkyls, ($C_2$–$C_6$)polyhydroxyalkyls, ($C_1$–$C_6$)alkoxy($C_1$–$C_6$)alkyls, cyano($C_1$–$C_6$)alkyls, aryls, benzyl, ($C_1$–$C_6$)amidoalkyls, tri($C_1$–$C_6$)alkylsilane($C_1$–$C_6$)alkyls, and ($C_1$–$C_6$)aminoalkyls in which the amine is protected with a radical chosen from ($C_1$–$C_6$)alkylcarbonyls, carbamyl, and ($C_1$–$C_6$) alkylsulphonyls; two of the radicals $R_8$, $R_9$ and $R_{10}$ can together also form, with the nitrogen atom to which they are attached, a saturated 5- or 6-membered ring or a ring containing at least one additional hetero atom, the ring being optionally substituted with a substituent chosen from halogen atoms, a hydroxyl group, ($C_1$–$C_6$)alkyls, ($C_1$–$C_6$)monohydroxyalkyls, ($C_2$–$C_6$)polyhydroxyalkyls, a nitro, a cyano, cyano($C_1$–$C_6$)alkyls, ($C_1$–$C_6$)alkoxys, tri($C_1$–$C_6$)alkylsilane($C_1$–$C_6$)alkyls, amido, aldehydo, carboxyl, keto($C_1$–$C_6$)alkyls, thio, ($C_1$–$C_6$)thioalkyls, ($C_1$–$C_6$)alkylthios, amino, and aminos protected with a radical chosen from ($C_1$–$C_6$) alkylcarbonyls, carbamyl, and ($C_1$–$C_6$) alkylsulphonyls; one of the radicals $R_8$, $R_9$ and $R_{10}$ can also be chosen from a second group Z which is identical to or different from the first group Z;

$R_{11}$ is a radical chosen from ($C_1$–$C_6$)alkyls; ($C_1$–$C_6$) monohydroxyalkyls; ($C_2$–$C_6$)polyhydroxyalkyls; aryls; benzyl; ($C_1$–$C_6$)aminoalkyls, ($C_1$–$C_6$) aminoalkyls in which the amine is protected with a radical chosen from ($C_1$–$C_6$)alkylcarbonyls, carbamyl, and ($C_1$–$C_6$)alkylsulphonyls; carboxy ($C_1$–$C_6$)alkyls; cyano($C_1$–$C_6$)alkyls; carbamyl ($C_1$–$C_6$)alkyls; ($C_1$–$C_6$)trifluoroalkyls; tri($C_1$–$C_6$) alkylsilane($C_1$–$C_6$)alkyls; ($C_1$–$C_6$) sulphonamidoalkyls; ($C_1$–$C_6$)alkylcarboxy($C_1$–$C_6$) alkyls; ($C_1$–$C_6$)alkylsulphinyl($C_1$–$C_6$)alkyls; ($C_1$–$C_6$)alkylsulphonyl($C_1$–$C_6$)alkyls; ($C_1$–$C_6$) alkylketo($C_1$–$C_6$)alkyls; N—($C_1$–$C_6$)alkylcarbamyl ($C_1$–$C_6$)alkyls; N—($C_1$–$C_6$)alkylsulphonamido ($C_1$–$C_6$)alkyls;

x and y are integers chosen from 0 and 1; with the provision that:
in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical $R_7$ is borne by the nitrogen atom of the unsaturated ring; or alternatively
2) when at least one of the ring members E, G, J and L represents a nitrogen atom to which the radical $R_7$ is attached;
in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is chosen from divalent atoms and when the radical $R_7$ is borne by the nitrogen atom of the unsaturated ring;
in the cationic groups of formula (IV):
when x=0, then the linker arm is attached to the nitrogen atom bearing the radicals $R_8$ to $R_{10}$,
when x=1, then two of the radicals $R_8$ to $R_{10}$ form, together with the nitrogen atom to which they are attached, a saturated 5- or 6-membered ring as defined above, and the linker arm D is borne by a carbon atom of the saturated ring;

$X^-$ is chosen from monovalent and divalent anions;
it being understood that:
the number of unsaturated cationic groups Z of formula (II) or (III) is at least equal to 1;
when at least one of $R_4$, $R_5$, $R'_4$, and $R'_5$, is chosen from Z groups in which the linker arm D represents an alkyl chain comprising a ketone function, then the ketone function is not directly attached to the nitrogen atom of the group —$NR_4R_5$ or —$NR'_4R'_5$.

2. A compound or salt according to claim 1 wherein the alkyl chains of said linker D comprise from 1 to 14 chosen atoms.

3. A compound or salt according to claim 1, wherein $X^-$ is chosen from chlorine, bromine, fluorine and iodine, a hydroxides hydrogenosulphate, and ($C_1$–$C_6$)alkyl sulphates.

4. A compound or salt according to claim 1, wherein said 5- or 6-membered saturated ring or ring containing one or more additional hetero atoms is chosen from pyrrolidine rings, piperidine rings, piperazine rings, and morpholine rings, said rings are unsubstituted or are optionally substituted with a substituent chosen from halogen atoms, hydroxyl, ($C_1$–$C_6$)alkyls, ($C_1$–$C_6$)monohydroxyalkyls, ($C_2$–$C_6$)polyhydroxyalkyls, nitro, cyano, cyano($C_1$–$C_6$) alkyls, ($C_1$–$C_6$)alkoxys, tri($C_1$–$C_6$)alkylsilane($C_1$–$C_6$) alkyls, amido, aldehydo, carboxyl, ($C_1$–$C_6$)alkylcarbonyls, thio, ($C_1$–$C_6$)thioalkyls, ($C_1$–$C_6$)alkylthios, amino, and amino protected with a group chosen from ($C_1$–$C_6$) alkylcarbonyls, carbamyl, and ($C_1$–$C_6$)alkylsulphonyls.

5. A compound or salt according to claim 1, wherein said rings in the unsaturated groups Z of formula (II) are chosen from pyrrole, imidazole, pyrazole, oxazole, thiazole and triazole rings.

6. A compound or salt according to claim 1, wherein said rings in the unsaturated groups Z of formula (III) are chosen from pyridine, pyrimidine, pyrazine, oxazine and triazine rings.

7. A compound or salt according to claim 1, chosen from:
3-[3-(2-aminophenylamino)propyl]-1-methyl-3H-imidazol-1-ium monochloride;
3-[2-(2-aminophenylamino)ethyl]-1-methyl-3H-imidazol-1-ium monochloride;
4-[2-(1-methyl-3H-imidazol-1-ium)ethoxy]-$N_2$-[2-(1-methyl-3H-imidazol-1-ium)ethyl]benzene-1,2-diamine dichloride;

3-[2-(2-amino-4-methylphenylamino)ethyl]-1-ethyl-3H-imidazol-1-ium monochloride;

3-[3-(2-aminophenylamino)propyl]-1-(3-trimethyl-ammonium-2-hydroxypropyl)-3H-imidazol-1-ium dichloride;

3-[3-(2-aminophenylamino)propyl]-1-(2-hydroxyethyl)-3H-imidazol-1-ium monobromide;

3-{[2-(2-aminophenylamino)ethylcarbamoyl]methyl}-1-methyl-3H-imidazol-1-ium monochloride;

1-[2-(2-amino-4-chlorophenylamino)ethyl]pyridinium monochloride;

3-[2-(2-amino-5-methoxyphenylamino)ethyl]-1-methyl-3H-imidazol-1-ium monochloride;

3-[2-(2-amino-5-methylsulphanylphenylamino)ethyl]-1-methyl-3H-imidazol-1-ium monochloride;

and the acid addition salts thereof.

8. The acid addition salt according to claim 1, wherein said acid addition salt is chosen from hydrochlorides, hydrobromides, sulphates, citrates, succinates, tartrates, lactates, and acetates.

9. An oxidation base, coupler, or self-oxidizing dye for the oxidation dyeing of keratin fibres comprising a compound of formula (I) below or an acid addition salt thereof:

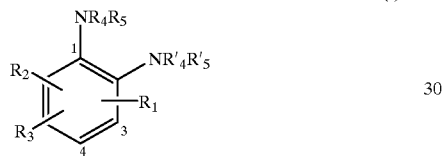

(I)

wherein:

$R^1$, $R^2$ and $R^3$, which may be identical or different, are chosen from a hydrogen atom; halogen atoms; Z groups; $(C_1-C_6)$alkylcarbonyls; amino$(C_1-C_6)$alkylcarbonyls; N—Z-amino$(C_1-C_6)$alkylcarbonyls; N—$(C_1-C_6)$alkylamino$(C_1-C_6)$alkylcarbonyls; N,N-di$(C_1-C_6)$alkylamino$(C_1-C_6)$alkylcarbonyls; amino$(C_1-C_6)$alkylcarbonyl$(C_1-C_6)$alkyls; N—Z-amino$(C_1-C_6)$alkylcarbonyl$(C_1-C_6)$alkyls; N—$(C_1-C_6)$alkylamino$(C_1-C_6)$alkylcarbonyl$(C_1-C_6)$alkyls; N,N-di$(C_1-C_6)$alkylamino$(C_1-C_6)$alkylcarbonyl$(C_1-C_6)$alkyls; carboxyl; $(C_1-C_6)$alkylcarboxyls; $(C_1-C_6)$alkylsulphonyls; aminosulphonyls; N—Z-aminosulphonyls; $(C_1-C_6)$N-alkylaminosulphonyls; N,N-di$(C_1-C_6)$alkylaminosulphonyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; carbamyl; N—$(C_1-C_6)$alkylcarbamyls; N,N-di$(C_1-C_6)$alkylcarbamyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$alkyls; $(C_1-C_6)$monohydroxyalkyls; $(C_2-C_6)$polyhydroxyalkyls; $(C_1-C_6)$alkoxy$(C_1-C_6)$-alkyls; $(C_1-C_6)$trifluoroalkyls; cyano; $OR_6$ and $SR_6$ groups; amino groups protected with a radical chosen from $(C_1-C_6)$alkylcarbonyls, $(C_1-C_6)$alkylcarboxyls, trifluoro$(C_1-C_6)$alkylcarbonyls, amino$(C_1-C_6)$alkylcarbonyls, N—Z-amino$(C_1-C_6)$alkylcarbonyls, N—$(C_1-C_6)$alkylamino$(C_1-C_6)$alkylcarbonyls, N,N-di$(C_1-C_6)$alkylamino$(C_1-C_6)$alkylcarbonyls, $(C_1-C_6)$alkylcarboxyls, carbamyl, N—$(C_1-C_6)$alkylcarbamyls, N,N-di$(C_1-C_6)$alkylcarbamyls, $(C_1-C_6)$alkylsulphonyls, aminosulphonyls, N—Z-aminosulphonyls, $(C_1-C_6)$N-alkylaminosulphonyls, N,N-di$(C_1-C_6)$alkylaminosulphonyls, thiocarbamyl, formyl, and Z groups, in which the linker arm D of the Z group comprises a ketone function directly attached to the nitrogen atom of the amino group; and $(C_1-C_6)$aminoalkyl in which the amine is substituted with at least one, identical or different radical, chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkyl-carbamyls, N,N-di$(C_1-C_6)$alkylcarbamyls, $(C_1-C_6)$alkylsulphonyls, formyl, trifluoro$(C1-C_6)$alkyl-carbonyls, $(C_1-C_6)$alkylcarboxyls, thiocarbamyl, and Z groups;

$R_6$ is a radical chosen from $(C_1-C_6)$alkyls; $(C_1-C_6)$monohydroxyalkyls; $(C_2-C_6)$polyhydroxyalkyls; Z groups; $(C_1-C_6)$alkoxy$(C_1-C_6)$alkyls; aryls; benzyl; carboxy$(C_1-C_6)$alkyls; $(C_1-C_6)$alkylcarboxy$(C_1-C_6)$alkyls; cyano$(C_1-C_6)$alkyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$trifluoroalkyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; $(C_1-C_6)$alkylsulphinyl$(C_1-C_6)$alkyls; $(C_1-C_6)$alkylsulphonyl$(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, formyl, trifluoro-$(C_1-C_6)$alkylcarbonyls, $(C_1-C_6)$alkylcarboxyls, carbamyl, N—$(C_1-C_6)$alkylcarbamyls, N,N-di-$(C_1-C_6)$alkylcarbamyls, thiocarbamyl and $(C_1-C_6)$alkylsulphonyls, and Z groups;

$R_4$, $R'_4$, $R_5$ and $R'_5$, which may be identical or different, are substituents chosen from a hydrogen atom; Z groups; $(C_1-C_6)$alkyls; $(C_1-C_6)$monohydroxyalkyls; $(C_2-C_6)$polyhydroxyalkyls; $(C_1-C_6)$alkoxy$(C_1-C_6)$alkyls; aryls; benzyl; cyano$(C_1-C_6)$alkyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; thiocarbamyl$(C_1-C_6)$alkyls; $(C_1-C_6)$trifluoroalkyls; $(C_1-C_6)$sulphoalkyls; $(C_1-C_6)$alkylcarboxy$(C_1-C_6)$alkyls; $(C_1-C_6)$alkylsulphinyl$(C_1-C_6)$alkyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$alkylcarbamyls, $(C_1-C_6)$alkylsulphonyls, formyl, trifluoro$(C_1-C_6)$alkylcarbonyls, $(C_1-C_6)$alkylcarboxyls, thiocarbamyl, and Z groups;

Z is chosen from unsaturated cationic groups of formulae (II) and (III) below, and the saturated cationic groups of formula (IV) below:

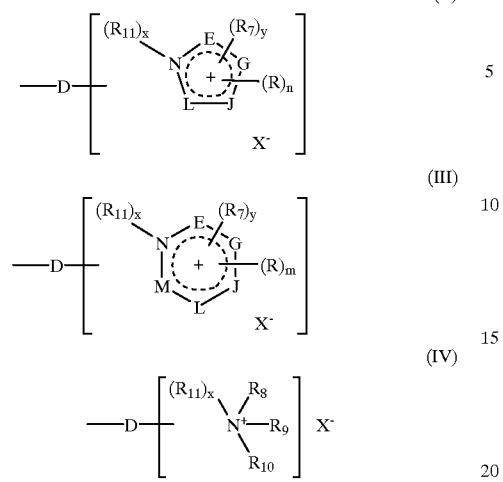

in which:
- D is a linker arm chosen from linear and branched alkyl chains, optionally interrupted by at least one hetero atom, such as oxygen, sulphur, and nitrogen atoms, and optionally substituted with at least one radical chosen from a hydroxyl group and $(C_1-C_6)$alkoxys, and which can optionally bear at least one ketone function;
- the ring members E, G, J, L and M, which may be identical or different, are chosen from carbon, oxygen, sulphur, and nitrogen atoms;
- n is chosen from the integers 0, 1, 2, 3, and 4;
- m is chosen from the integers 0, 1, 2, 3, 4, and 5;
- the radicals R, which may be identical or different, are chosen from a second group Z which is identical to or different from the first group Z, a halogen atom, a hydroxyl, $(C_1-C_6)$alkyls, $(C_1-C_6)$monohydroxyalkyls, $(C_2-C_6)$polyhydroxyalkyls, a nitro, a cyano, cyano$(C_1-C_6)$alkyls, $(C_1-C_6)$alkoxys, tri$(C_1-C_6)$alkylsilane$(C_1-C_6)$alkyls, amido, aldehydo, carboxyl, $(C_1-C_6)$alkylcarbonyls, thio, $(C_1-C_6)$thioalkyls, $(C_1-C_6)$alkylthios, amino, aminos protected with a radical chosen from $(C_1-C_6)$alkylcarbonyls, carbamyls and $(C_1-C_6)$alkylsulphonyls; NHR" groups, NR"R"' groups in which R" and R"', which may be identical or different, are chosen from $(C_1-C_6)$alkyl radicals, $(C_1-C_6)$monohydroxyalkyl radicals, and $(C_2-C_6)$polyhydroxyalkyl radicals;
- $R_7$ is a radical chosen from $(C_1-C_6)$alkyls, $(C_1-C_6)$monohydroxyalkyls, $(C_2-C_6)$polyhydroxyalkyls, cyano$(C_1-C_6)$alkyls, tri$(C_1-C_6)$alkylsilane$(C_1-C_6)$alkyls, $(C_1-C_6)$alkoxy$(C_1-C_6)$alkyls, carbamyl-$(C_1-C_6)$alkyls, $(C_1-C_6)$alkylcarboxy$(C_1-C_6)$alkyls, benzyl and a second group Z which is identical to or different from the first group Z;
- $R_8$, $R_9$ and $R_{10}$, which may be identical or different, are radicals chosen from $(C_1-C_6)$alkyls, $(C_1-C_6)$monohydroxyalkyls, $(C_2-C_6)$polyhydroxyalkyls, $(C_1-C_6)$alkoxy$(C_1-C_6)$alkyls, cyano$(C_1-C_6)$alkyls, aryls, benzyl, $(C_1-C_6)$amidoalkyls, tri$(C_1-C_6)$alkylsilane$(C_1-C_6)$alkyls, and $(C_1-C_6)$aminoalkyls in which the amine is protected with a radical chosen from $(C_1-C_6)$alkylcarbonyls, carbamyl, and $(C_1-C_6)$alkylsulphonyls; two of the radicals $R_8$, $R_9$ and $R_{10}$ can together also form, with the nitrogen atom to which they are attached, a saturated 5- or 6-membered ring or a ring containing at least one additional hetero atom, the ring being optionally substituted with a substituent chosen from halogen atoms, a hydroxyl group, $(C_1-C_6)$alkyls, $(C_1-C_6)$monohydroxyalkyls, $(C_2-C_6)$polyhydroxyalkyls, a nitro, a cyano, cyano$(C_1-C_6)$alkyls, $(C_1-C_6)$alkoxys, tri$(C_1-C_6)$alkylsilane$(C_1-C_6)$alkyls, amido, aldehydo, carboxyl, keto$(C_1-C_6)$alkyls, thio, $(C_1-C_6)$thioalkyls, $(C_1-C_6)$alkylthios, amino, and aminos protected with a radical chosen from $(C_1-C_6)$alkylcarbonyls, carbamyl, and $(C_1-C_6)$alkylsulphonyls; one of the radicals $R_8$, $R_9$ and $R_{10}$ can also be chosen from a second group Z which is identical to or different from the first group Z;
- $R_{11}$ is a radical chosen from $(C_1-C_6)$alkyls; $(C_1-C_6)$monohydroxyalkyls; $(C_2-C_6)$polyhydroxyalkyls; aryls; benzyl; $(C_1-C_6)$aminoalkyls, $(C_1-C_6)$aminoalkyls in which the amine is protected with a radical chosen from $(C_1-C_6)$alkylcarbonyls, carbamyl, and $(C_1-C_6)$alkylsulphonyls; carboxy$(C_1-C_6)$alkyls; cyano$(C_1-C_6)$alkyls; carbamyl$(C_1-C_6)$alkyls; $(C_1-C_6)$trifluoroalkyls; tri$(C_1-C_6)$alkylsilane$(C_1-C_6)$alkyls; $(C_1-C_6)$sulphonamidoalkyls; $(C_1-C_6)$alkylcarboxy$(C_1-C_6)$alkyls; $(C_1-C_6)$alkylsulphinyl$(C_1-C_6)$alkyls; $(C_1-C_6)$alkylsulphonyl$(C_1-C_6)$alkyls; $(C_1-C_6)$alkylketo$(C_1-C_6)$alkyls; N—$(C_1-C_6)$alkylcarbamyl$(C_1-C_6)$alkyls; N—$(C_1-C_6)$alkylsulphonamido$(C_1-C_6)$alkyls;
- x and y are integers chosen from 0 and 1; with the provision that:
  in the unsaturated cationic groups of formula (II):
    when x=0, the linker arm D is attached to the nitrogen atom,
    when x=1, the linker arm D is attached to one of the ring members E, G, J or L,
    y can take the value 1 only:
      1) when the ring members E, G, J and L simultaneously represent a carbon atom and when the radical $R_7$ is borne by the nitrogen atom of the unsaturated ring; or alternatively
      2) when at least one of the ring members E, G, J and L represents a nitrogen atom to which the radical $R_7$ is attached;
  in the unsaturated cationic groups of formula (III):
    when x=0, the linker arm D is attached to the nitrogen atom,
    when x=1, the linker arm D is attached to one of the ring members E, G, J, L or M,
    y can take the value 1 only when at least one of the ring members E, G, J, L and M is chosen from divalent atoms and when the radical $R_7$ is borne by the nitrogen atom of the unsaturated ring;
  in the cationic groups of formula (IV):
    when x=0, then the linker arm is attached to the nitrogen atom bearing the radicals $R_8$ to $R_{10}$,
    when x=1, then two of the radicals $R_8$ to $R_{10}$ form, together with the nitrogen atom to which they are attached, a saturated 5- or 6-membered ring as defined above, and the linker arm D is borne by a carbon atom of the saturated ring;
- $X^-$ is chosen from monovalent and divalent anions;
- it being understood that:
  the number of unsaturated cationic groups Z of formula (II) or (III) is at least equal to 1;

when at least one of $R_4$, $R_5$, $R'_4$, and $R'_5$, is chosen from Z groups in which the linker arm D represents an alkyl chain comprising a ketone function, then the ketone function is not directly attached to the nitrogen atom of the group —$NR_4R_5$ or —$NR'_4R'_5$.

10. A composition for the oxidation dyeing of keratin fibres, comprising a medium suitable for dyeing and at least one ingredient chosen from compounds of formula (I), below, and the acid addition salts thereof:

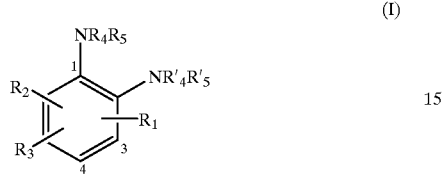

(I)

wherein:

$R^1$, $R^2$ and $R^3$, which may be identical or different, are chosen from a hydrogen atom; halogen atoms; Z groups; $(C_1-C_6)$alkylcarbonyls; amino$(C_1-C_6)$alkylcarbonyls; N—Z-amino$(C_1-C_6)$alkylcarbonyls; N—$(C_1-C_6)$alkylamino$(C_1-C_6)$alkylcarbonyls; N,N-di$(C_1-C_6)$alkylamino$(C_1-C_6)$alkylcarbonyls; amino$(C_1-C_6)$alkylcarbonyl$(C_1-C_6)$alkyls; N—Z-amino$(C_1-C_6)$alkylcarbonyl$(C_1-C_6)$alkyls; N—$(C_1-C_6)$alkylamino$(C_1-C_6)$alkylcarbonyl$(C_1-C_6)$alkyls; N,N-di$(C_1-C_6)$alkylamino$(C_1-C_6)$alkylcarbonyl$(C_1-C_6)$alkyls; carboxyl; $(C_1-C_6)$alkylcarboxyls; $(C_1-C_6)$alkylsulphonyls; aminosulphonyls; N—Z-aminosulphonyls; $(C_1-C_6)$N-alkylaminosulphonyls; N,N-di$(C_1-C_6)$alkylaminosulphonyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; carbamyl; N—$(C_1-C_6)$alkylcarbamyls; N,N-di$(C_1-C_6)$alkylcarbamyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$alkyls; $(C_1-C_6)$monohydroxyalkyls; $(C_2-C_6)$polyhydroxyalkyls; $(C_1-C_6)$alkoxy$(C_1-C_6)$-alkyls; $(C_1-C_6)$trifluoroalkyls; cyano; $OR_6$ and $SR_6$ groups; amino groups protected with a radical chosen from $(C_1-C_6)$alkylcarbonyls, $(C_1-C_6)$alkylcarboxyls, trifluoro$(C_1-C_6)$alkylcarbonyls, amino$(C_1-C_6)$alkylcarbonyls, N—Z-amino$(C_1-C_6)$alkylcarbonyls, N—$(C_1-C_6)$alkylamino$(C_1-C_6)$alkylcarbonyls, N,N-di$(C_1-C_6)$alkylamino$(C_1-C_6)$alkylcarbonyls, $(C_1-C_6)$alkylcarboxyls, carbamyl, N—$(C_1-C_6)$alkylcarbamyls, N,N-di$(C_1-C_6)$alkylcarbamyls, $(C_1-C_6)$alkylsulphonyls, aminosulphonyls, N—Z-aminosulphonyls, $(C_1-C_6)$N-alkylaminosulphonyls, N,N-di$(C_1-C_6)$alkylaminosulphonyls, thiocarbamyl, formyl, and Z groups, in which the linker arm D of the Z group comprises a ketone function directly attached to the nitrogen atom of the amino group; and $(C_1-C_6)$aminoalkyl in which the amine is substituted with at least one, identical or different radical, chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkyl-carbamyls, N,N-di$(C_1-C_6)$alkylcarbamyls, $(C_1-C_6)$alkylsulphonyls, formyl, trifluoro$(C_1-C_6)$alkyl-carbonyls, $(C_1-C_6)$alkylcarboxyls, thiocarbamyl, and Z groups;

$R_6$ is a radical chosen from $(C_1-C_6)$alkyls; $(C_1-C_6)$monohydroxyalkyls; $(C_2-C_6)$polyhydroxyalkyls; Z groups; $(C_1-C_6)$alkoxy$(C_1-C_6)$alkyls; aryls; benzyl; carboxy$(C_1-C_6)$alkyls; $(C_1-C_6)$alkylcarboxy$(C_1-C_6)$alkyls; cyano$(C_1-C_6)$alkyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$trifluoroalkyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; $(C_1-C_6)$alkylsulphinyl$(C_1-C_6)$alkyls; $(C_1-C_6)$alkylsulphonyl$(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, formyl, trifluoro-$(C_1-C_6)$alkylcarbonyls, $(C_1-C_6)$alkylcarboxyls, carbamyl, N—$(C_1-C_6)$alkylcarbamyls, N,N-di-$(C_1-C_6)$alkylcarbamyls, thiocarbamyl and $(C_1-C_6)$alkylsulphonyls, and Z groups;

$R_4$, $R'_4$, $R_5$ and $R'_5$, which may be identical or different, are substituents chosen from a hydrogen atom; Z groups; $(C_1-C_6)$alkyls; $(C_1-C_6)$monohydroxyalkyls; $(C_2-C_6)$polyhydroxyalkyls; $(C_1-C_6)$alkoxy$(C_1-C_6)$alkyls; aryls; benzyl; cyano$(C_1-C_6)$alkyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; thiocarbamyl$(C_1-C_6)$alkyls; $(C_1-C_6)$trifluoroalkyls; $(C_1-C_6)$sulphoalkyls; $(C_1-C_6)$alkylcarboxy$(C_1-C_6)$alkyls; $(C_1-C_6)$alkylsulphinyl$(C_1-C_6)$alkyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$alkylcarbamyls, $(C_1-C_6)$alkylsulphonyls, formyl, trifluoro$(C_1-C_6)$alkylcarbonyls, $(C_1-C_6)$alkylcarboxyls, thiocarbamyl, and Z groups;

Z is chosen from unsaturated cationic groups of formulae (II) and (III) below, and the saturated cationic groups of formula (IV) below:

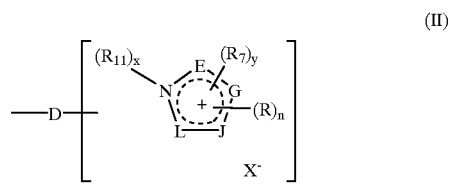

(II)

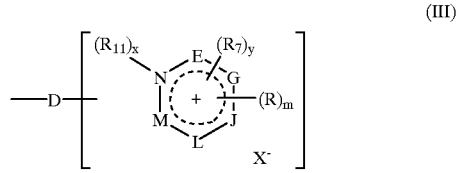

(III)

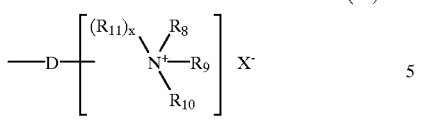

in which:
D is a linker arm chosen from linear and branched alkyl chains, optionally interrupted by at least one hetero atom, such as oxygen, sulphur, and nitrogen atoms, and optionally substituted with at least one radical chosen from a hydroxyl group and $(C_1-C_6)$alkoxys, and which can optionally bear at least one ketone function;
the ring members E, G, J, L and M, which may be identical or different, are chosen from carbon, oxygen, sulphur, and nitrogen atoms;
n is chosen from the integers 0, 1, 2, 3, and 4;
m is chosen from the integers 0, 1, 2, 3, 4, and 5;
the radicals R, which may be identical or different, are chosen from a second group Z which is identical to or different from the first group Z, a halogen atom, a hydroxyl, $(C_1-C_6)$alkyls, $(C_1-C_6)$monohydroxyalkyls, $(C_2-C_6)$polyhydroxyalkyls, a nitro, a cyano, cyano$(C_1-C_6)$alkyls, $(C_1-C_6)$alkoxys, tri$(C_1-C_6)$alkylsilane$(C_1-C_6)$alkyls, amido, aldehydo, carboxyl, $(C_1-C_6)$alkylcarbonyls, thio, $(C_1-C_6)$thioalkyls, $(C_1-C_6)$alkylthios, amino, aminos protected with a radical chosen from $(C_1-C_6)$alkylcarbonyls, carbamyls and $(C_1-C_6)$alkylsulphonyls; NHR" groups, NR"R"' groups in which R" and R"', which may be identical or different, are chosen from $(C_1-C_6)$alkyl radicals, $(C_1-C_6)$monohydroxyalkyl radicals, and $(C_2-C_6)$polyhydroxyalkyl radicals;
$R_7$ is a radical chosen from $(C_1-C_6)$alkyls, $(C_1-C_6)$monohydroxyalkyls, $(C_2-C_6)$polyhydroxyalkyls, cyano$(C_1-C_6)$alkyls, tri$(C_1-C_6)$alkylsilane$(C_1-C_6)$alkyls, $(C_1-C_6)$alkoxy$(C_1-C_6)$alkyls, carbamyl-$(C_1-C_6)$alkyls, $(C_1-C_6)$alkylcarboxy$(C_1-C_6)$alkyls, benzyl and a second group Z which is identical to or different from the first group Z;
$R_8$, $R_9$ and $R_{10}$, which may be identical or different, are radicals chosen from $(C_1-C_6)$alkyls, $(C_1-C_6)$monohydroxyalkyls, $(C_2-C_6)$polyhydroxyalkyls, $(C_1-C_6)$alkoxy$(C_1-C_6)$alkyls, cyano$(C_1-C_6)$alkyls, aryls, benzyl, $(C_1-C_6)$amidoalkyls, tri$(C_1-C_6)$alkylsilane$(C_1-C_6)$alkyls, and $(C_1-C_6)$aminoalkyls in which the amine is protected with a radical chosen from $(C_1-C_6)$alkylcarbonyls, carbamyl, and $(C_1-C_6)$alkylsulphonyls; two of the radicals $R_8$, $R_9$ and $R_{10}$ can together also form, with the nitrogen atom to which they are attached, a saturated 5- or 6-membered ring or a ring containing at least one additional hetero atom, the ring being optionally substituted with a substituent chosen from halogen atoms, a hydroxy group, $(C_1-C_6)$alkyls, $(C_1-C_6)$monohydroxyalkyls, $(C_2-C_6)$polyhydroxyalkyls, a nitro, a cyano, cyano$(C_1-C_6)$alkyls, $(C_1-C_6)$alkoxys, tri$(C_1-C_6)$alkylsilane$(C_1-C_6)$alkyls, amido, aldehydo, carboxyl, keto$(C_1-C_6)$alkyls, thio, $(C_1-C_6)$thioalkyls, $(C_1-C_6)$alkylthios, amino, and aminos protected with a radical chosen from $(C_1-C_6)$alkylcarbonyls, carbamyl, and $(C_1-C_6)$alkylsulphonyls; one of the radicals $R_8$, $R_9$ and $R_{10}$ can also be chosen from a second group Z which is identical to or different from the first group Z;
$R_{11}$ is a radical chosen from $(C_1-C_6)$alkyls; $(C_1-C_6)$monohydroxyalkyls; $(C_2-C_6)$polyhydroxyalkyls; aryls; benzyl; $(C_1-C_6)$aminoalkyls, $(C_1-C_6)$aminoalkyls in which the amine is protected with a radical chosen from $(C_1-C_6)$alkylcarbonyls, carbamyl, and $(C_1-C_6)$alkylsulphonyls; carboxy$(C_1-C_6)$alkyls; cyano$(C_1-C_6)$alkyls; carbamyl$(C_1-C_6)$alkyls; $(C_1-C_6)$trifluoroalkyls; tri$(C_1-C_6)$alkylsilane$(C_1-C_6)$alkyls; $(C_1-C_6)$sulphonamidoalkyls; $(C_1-C_6)$alkylcarboxy$(C_1-C_6)$alkyls; $(C_1-C_6)$alkylsulphinyl$(C_1-C_6)$alkyls; $(C_1-C_6)$alkylsulphonyl$(C_1-C_6)$alkyls; $(C_1-C_6)$alkylketo$(C_1-C_6)$alkyls; N—$(C_1-C_6)$alkylcarbamyl$(C_1-C_6)$alkyls; N—$(C_1-C_6)$alkylsulphonamido$(C_1-C_6)$alkyls;
x and y are integers chosen from 0 and 1; with the provision that:
in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical $R_7$ is borne by the nitrogen atom of the unsaturated ring; or alternatively
2) when at least one of the ring members E, G, J and L represents a nitrogen atom to which the radical $R_7$ is attached;
in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is chosen from divalent atoms and when the radical $R_7$ is borne by the nitrogen atom of the unsaturated ring;
in the cationic groups of formula (IV):
when x=0, then the linker arm is attached to the nitrogen atom bearing the radicals $R_8$ to $R_{10}$,
when x=1, then two of the radicals $R_8$ to $R_{10}$ form, together with the nitrogen atom to which they are attached, a saturated 5- or 6-membered ring as defined above, and the linker arm D is borne by a carbon atom of the saturated ring;
$X^-$ is chosen from monovalent and divalent anions;
it being understood that:
the number of unsaturated cationic groups Z of formula (II) or (III) is at least equal to 1;
when at least one of $R_4$, $R_5$, $R'_4$, and $R'_5$, is chosen from Z groups in which the linker arm D represents an alkyl chain comprising a ketone function, then the ketone function is not directly attached to the nitrogen atom of the group —$NR_4R_5$ or —$NR'_4R'_5$.

11. A dye composition according to claim 10, wherein said at least one ingredient is present in said dye composition in an amount ranging from 0.0005 to 12% by weight relative to the total weight of the dye composition.

12. A dye composition according to claim 11, wherein said at least one ingredient is present in said dye composition in an amount ranging from 0.005 to 6% by weight relative to the total weight of the dye cornposition.

13. A dye composition according to claim 11, further comprising at least one oxidation base chosen from para-phenylenediamines, bis(phenyl)alkylenediamines, para-aminophenols, ortho-aminophenols, and heterocyclic bases which are different from said at least one ingredient.

14. A dye composition according to claim 13, wherein said para-phenylenediamines are chosen from para-phenylenediamine, para-tolylene-diamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N—(β-hydroxypropyl)-para-phenylene-diamine, 2-hydroxymethyl-para-phenylenediamine, N,N-dimethyl-3-methyl-para-phenylenediamine, N-ethyl-N—(β-hydroxyethyl)-para-phenylenediamine, N—(β,γ-dihydroxypropyl)-para-phenylenediamine, N—(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N—(β-methoxyethyl)-para-phenylenediamine, and the acid addition salts thereof.

15. A dye composition according to claim 13, wherein said bis(phenyl)alkylenediamines are chosen from N,N'-bis(β-hydroxyethyl)-N,N'-bis(4'-aminophenyl)-1,3-diaminopropanol, N,N'-bis(β-hydroxy-ethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)-tetramethylenediamine, N,N'-bis(ethyl)-N,N'-bis(4'-amino-3'-methylphenyl)ethylenediamine, and 1,8-bis(2,5-diaminophenoxy)-3,5-dioxaoctane, and the acid addition salts thereof.

16. A dye composition according to claim 13, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and 4-amino-2-fluorophenol, and the acid addition salts thereof.

17. A dye composition according to claim 13, wherein said ortho-aminophenols are chosen from 2-aminophenol, 2-amino-5-methylphenol, 2-amino-6-methylphenol, and 5-acetamid-2-aminophenol, and the acid addition salts thereof.

18. A dye composition according to claim 13, wherein said heterocyclic bases are chosen from pyridine derivatives, pyrimidine derivatives and pyrazole derivatives.

19. A dye composition according to claim 13, wherein said at least one oxidation base is present in said dye composition an amount ranging from 0.0005 to 12% by weight relative to the total weight of said dye composition.

20. A dye composition according to claim 19, wherein said at least one oxidation base is present in said dye composition in an amount ranging from 0.005 to 6% by weight relative to the total weight of the dye composition.

21. A dye composition according to claim 10, further comprising at least one coupler chosen from meta-phenylenediamines, meta-aminophenols, meta-diphenols, and heterocyclic couplers.

22. A dye composition according to claim 21, wherein said at least one coupler is chosen from 2-methyl-5-aminophenol, 5-N—(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the acid addition salts thereof.

23. A dye composition according to claim 21, wherein said at least one coupler is present in said dye composition in an amount ranging from 0.0001 to 10% by weight relative to the total weight of the dye composition.

24. A dye composition according to claim 10, wherein said at least one coupler is present in said dye composition in an amount ranging from 0.005 to 5% by weight relative to the total weight of the dye composition.

25. A dye composition according to claim 10, wherein said acid addition salts are chosen from hydrochlorides, hydrobromides, sulphates, citrates, succinates, tartrates, lactates and acetates.

26. A process for the oxidation dyeing of keratin fibres, comprising applying at least one dye composition to said fibres in the presence of either air or an oxidizing agent, for a period which is sufficient to develop desired coloration, wherein said at least one dye composition comprises at least one ingredient chosen from compounds of formula (I), below, and the acid addition salts thereof:

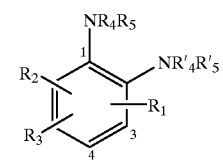

(I)

wherein:
$R^1$, $R^2$ and $R^3$, which may be identical or different, are chosen from a hydrogen atom; halogen atoms; Z groups; $(C_1-C_6)$alkylcarbonyls; amino$(C_1-C_6)$alkylcarbonyls; N—Z-amino$(C_1-C_6,)$alkylcarbonyls; N—$(C_1-C_6)$alkylamino$(C_1-C_6)$alkylcarbonyls; N,N-di$(C_1-C_6)$alkylamino$(C_1-C_6)$alkylcarbonyls; amino$(C_1-C_6)$alkylcarbonyl$(C_1-C_6)$alkyls; N—Z-amino$(C_1-C_6)$alkylcarbonyl$(C_1-C_6)$alkyls; N—$(C_1-C_6)$alkylamino$(C_1-C_6)$alkylcarbonyl$(C_1-C_6)$alkyls; N,N-di$(C_1-C_6)$alkylamino$(C_1-C_6)$alkylcarbonyl$(C_1-C_6)$alkyls; carboxyl; $(C_1-C_6)$alkylcarboxyls; $(C_1-C_6)$alkylsulphonyls; aminosulphonyls; N—Z-aminosulphonyls; $(C_1-C_6)$N-alkylaminosulphonyls; N,N-di$(C_1-C_6)$alkylaminosulphonyls; $(C_1-C_6)$aminosulphonylalkyls; $(C_1-C_6)$N—Z-aminosulphonylalkyls; N—$(C_1-C_6)$alkylaminosulphonyl$(C_1-C_6)$alkyls; N,N-di$(C_1-C_6)$alkylaminosulphonyl$(C_1-C_6)$alkyls; carbamyl; N—$(C_1-C_6)$alkylcarbamyls; N,N-di$(C_1-C_6)$alkylcarbamyls; carbamyl$(C_1-C_6)$alkyls; N—$(C_1-C_6)$alkylcarbamyl$(C_1-C_6)$alkyls; N,N-di$(C_1-C_6)$alkylcarbamyl$(C_1-C_6)$alkyls; $(C_1-C_6)$alkyls; $(C_1-C_6)$monohydroxyalkyls; $(C_2-C_6)$polyhydroxyalkyls; $(C_1-C_6)$alkoxy$(C_1-C_6)$-alkyls; $(C_1-C_6)$trifluoroalkyls; cyano; $OR_6$ and $SR_6$ groups; amino groups protected with a radical chosen from $(C_1-C_6)$alkylcarbonyls, $(C_1-C_6)$alkylcarboxyls, trifluoro$(C_1-C_6)$ alkylcarbonyls, amino$(C_1-C_6)$alkylcarbonyls, N—Z-amino$(C_1-C_6)$alkylcarbonyls, N—$(C_1-C_6)$alkylamino $(C_1-C_6)$alkylcarbonyls, N,N-di$(C_1-C_6)$alkylamino $(C_1-C_6)$alkylcarbonyls, $(C_1-C_6)$alkylcarboxyls, carbamyl, N—$(C_1-C_6)$alkylcarbamyls, N,N-di$(C_1-C_6)$ alkylcarbamyls, $(C_1-C_6)$alkylsulphonyls, aminosulphonyls, N—Z-aminosulphonyls, $(C_1-C_6)$N-alkylaminosulphonyls, N,N-di$(C_1-C_6)$ alkylaminosulphonyls, thiocarbamyl, formyl, and Z groups, in which the linker arm D of the Z group comprises a ketone function directly attached to the nitrogen atom of the amino group; and $(C_1-C_6)$ aminoalkyl in which the amine is substituted with at least one, identical or different radical, chosen from $(C_1-C_6)$alkyls, $(C_1-C_6)$monohydroxyalkyls, $(C_2-C_6)$ polyhydroxyalkyls, $(C_1-C_6)$alkylcarbonyls, carbamyl, N—$(C_1-C_6)$alkyl-carbamyls, N,N-di$(C_1-C_6)$ alkylcarbamyls, $(C_1-C_6)$alkylsulphonyls, formyl, trifluoro$(C_1-C_6)$alkyl-carbonyls, $(C_1-C_6)$ alkylcarboxyls, thiocarbamyl, and Z groups;

$R_6$ is a radical chosen from $(C_1-C_6)$alkyls; $(C_1-C_6)$ monohydroxyalkyls; $(C_2-C_6)$polyhydroxyalkyls; Z groups; $(C_1-C_6)$alkoxy$(C_1-C_6)$alkyls; aryls; benzyl; carboxy$(C_1-C_6)$alkyls; $(C_1-C_6)$alkylcarboxy$(C_1-C_6)$ alkyls; cyano$(C_1-C_6)$alkyls; carbamyl$(C_1-C_6)$alkyls; N—$(C_1-C_6)$alkylcarbamyl$(C_1-C_6)$alkyls; N,N-di $(C_1-C_6)$alkylcarbamyl$(C_1-C_6)$alkyls; $(C_1-C_6)$ trifluoroalkyls; $(C_1-C_6)$aminosulphonylalkyls; $(C_1-C_6)$N—Z-aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; $(C_1-C_6)$ alkylsulphinyl$(C_1-C_6)$alkyls; $(C_1-C_6)$alkylsulphonyl $(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$ monohydroxyalkyls, $(C_2-C_6)$polyhydroxyalkyls, $(C_1-C_6)$alkylcarbonyls, formyl, trifluoro-$(C_1-C_6)$ alkylcarbonyls, $(C_1-C_6)$alkylcarboxyls, carbamyl, N—$(C_1-C_6)$alkylcarbamyls, N,N-di-$(C_1-C_6)$ alkylcarbamyls, thiocarbamyl and $(C_1-C_6)$ alkylsulphonyls, and Z groups;

$R_4$, $R'_4$, $R_5$ and $R'_5$, which may be identical or different, are substituents chosen from a hydrogen atom; Z groups; $(C_1-C_6)$alkyls; $(C_1-C_6)$monohydroxyalkyls; $(C_2-C_6)$polyhydroxyalkyls; $(C_1-C_6)$alkoxy$(C_1-C_6)$ alkyls; aryls; benzyl; cyano$(C_1-C_6)$alkyls; carbamyl $(C_1-C_6)$alkyls; N—$(C_1-C_6)$alkylcarbamyl$(C_1-C_6)$ alkyls; N,N-di$(C_1-C_6)$alkylcarbamyl$(C_1-C_6)$alkyls; thiocarbamyl$(C_1-C_6)$alkyls; $(C_1-C_6)$trifluoroalkyls; $(C_1-C_6)$sulphoalkyls; $(C_1-C_6)$alkylcarboxy$(C_1-C_6)$ alkyls; $(C_1-C_6)$alkylsulphinyl$(C_1-C_6)$alkyls; $(C_1-C_6)$ aminosulphonylalkyls; $(C_1-C_6)$N—Z-aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; $(C_1-C_6)$ alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$ alkylcarbamyls, $(C_1-C_6)$alkylsulphonyls, formyl, trifluoro$(C_1-C_6)$alkylcarbonyls, $(C_1-C_6)$ alkylcarboxyls, thiocarbamyl, and Z groups;

Z is chosen from unsaturated cationic groups of formulae (II) and (III) below, and the saturated cationic groups of formula (IV) below:

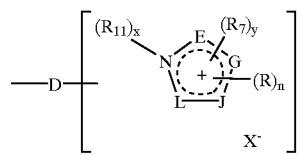

(II)

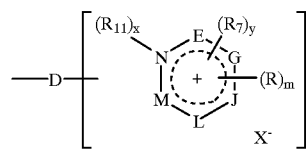

(III)

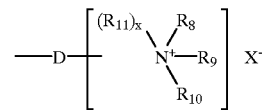

(IV)

in which:

D is a linker arm chosen from linear and branched alkyl chains, optionally interrupted by at least one hetero atom, such as oxygen, sulphur, and nitrogen atoms, and optionally substituted with at least one radical chosen from a hydroxyl group and $(O_1-C_6)$alkoxys, and which can optionally bear at least one ketone function;

the ring members E, G, J, L and M, which may be identical or different, are chosen from carbon, oxygen, sulphur, and nitrogen atoms;

n is chosen from the integers 0, 1, 2, 3, and 4;

m is chosen from the integers 0, 1, 2, 3, 4, and 5;

the radicals R, which may be identical or different, are chosen from a second group Z which is identical to or different from the first group Z, a halogen atom, a hydroxyl, $(C_1-C_6)$alkyls, $(C_1-C_6)$ monohydroxyalkyls, $(C_2-C_6)$polyhydroxyalkyls, a nitro, a cyano, cyano$(C_1-C_6)$alkyls, $(C_1-C_6)$alkoxys, tri$(C_1-C_6)$alkylsilane$(C_1-C_6)$alkyls, amido, aldehydo, carboxyl, $(C_1-C_6)$alkylcarbonyls, thio, $(C_1-C_6)$thioalkyls, $(C_1-C_6)$alkylthios, amino, aminos protected with a radical chosen from $(C_1-C_6)$ alkylcarbonyls, carbamyls and $(C_1-C_6)$ alkylsulphonyls; NHR"groups, NR"R"' groups in which R" and R"', which may be identical or different, are chosen from $(C_1-C_6)$alkyl radicals, $(C_1-C_6)$monohydroxyalkyl radicals, and $(C_2-C_6)$ polyhydroxyalkyl radicals;

$R_7$ is a radical chosen from $(C_1-C_6)$alkyls, $(C_1-C_6)$ monohydroxyalkyls, $(C_2-C_6)$polyhydroxyalkyls, cyano$(C_1-C_6)$alkyls, tri$(C_1-C_6)$alkylsilane$(C_1-C_6)$ alkyls, $(C_1-C_6)$alkoxy$(C_1-C_6)$alkyls, carbamyl-$(C_1-C_6)$alkyls, $(C_1-C_6)$alkylcarboxy$(C_1-C_6)$alkyls, benzyl and a second group Z which is identical to or different from the first group Z;

$R_8$, $R_9$ and $R_{10}$, which may be identical or different, are radicals chosen from $(C_1-C_6)$alkyls, $(C_1-C_6)$ monohydroxyalkyls, $(C_2-C_6)$polyhydroxyalkyls, $(C_1-C_6)$alkoxy$(C_1-C_6)$alkyls, cyano$(C_1-C_6)$alkyls, aryls, benzyl, $(C_1-C_6)$amidoalkyls, tri$(C_1-C_6)$ alkylsilane$(C_1-C_6)$alkyls, and $(C_1-C_6)$aminoalkyls in which the amine is protected with a radical chosen from (C$_1$–C$_6$)alkylcarbonyls, carbamyl, and (C$_1$–C$_6$) alkylsulphonyls; two of the radicals R$_8$, R$_9$ and R$_{10}$ can together also form, with the nitrogen atom to which they are attached, a saturated 5- or 6-membered ring or a ring containing at least one additional hetero atom, the ring being optionally substituted with a substituent chosen from halogen atoms, a hydroxyl group, (C$_1$–C$_6$) alkyls, (C$_1$–C$_6$)monohydroxyalkyls, (C$_2$–C$_6$)polyhydroxyalkyls, a nitro, a cyano, cyano(C$_1$–C$_6$)alkyls, (C$_1$–C$_6$)alkoxys, tri(C$_1$–C$_6$)alkylsilane(C$_1$–C$_6$)alkyls, amido, aldehydo, carboxyl, keto(C$_1$–C$_6$)alkyls, thio, (C$_1$–C$_6$)thioalkyls, (C$_1$–C$_6$)alkylthios, amino, and aminos protected with a radical chosen from (C$_1$–C$_6$) alkylcarbonyls, carbamyl, and (C$_1$–C$_6$) alkylsulphonyls; one of the radicals R$_8$, R$_9$ and R$_{10}$ can also be chosen from a second group Z which is identical to or different from the first group Z;

R$_{11}$ is a radical chosen from (C$_1$–C$_6$)alkyls; (C$_1$–C$_6$) monohydroxyalkyls; (C$_2$–C$_6$)polyhydroxyalkyls; aryls; benzyl; (C$_1$–C$_6$)aminoalkyls, (C$_1$–C$_6$) aminoalkyls in which the amine is protected with a radical chosen from (C$_1$–C$_6$)alkylcarbonyls, carbamyl, and (C$_1$–C$_6$)alkylsulphonyls; carboxy (C$_1$–C$_6$)alkyls; cyano(C$_1$–C$_6$)alkyls; carbamyl (C$_1$–C$_6$)alkyls; (C$_1$–C$_6$)trifluoroalkyls; tri(C$_1$–C$_6$) alkylsilane(C$_1$–C$_6$)alkyls; (C$_1$–C$_6$) sulphonamidoalkyls; (C$_1$–C$_6$)alkylcarboxy(C$_1$–C$_6$)alkyls; (C$_1$–C$_6$)alkylsulphinyl(C$_1$–C$_6$)alkyls; (C$_1$–C$_6$)alkylsulphonyl(C$_1$–C$_6$)alkyls; (C$_1$–C$_6$) alkylketo(C$_1$–C$_6$)alkyls; N—(C$_1$–C$_6$)alkylcarbamyl (C$_1$–C$_6$)alkyls; N—(C$_1$–C$_6$)alkylsulphonamido (C$_1$–C$_6$)alkyls;

x and y are integers chosen from 0 and 1; with the provision that:

in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical R$_7$ is borne by the nitrogen atom of the unsaturated ring; or alternatively
2) when at least one of the ring members E, G, J and L represents a nitrogen atom to which the radical R$_7$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is chosen from divalent atoms and when the radical R$_7$ is borne by the nitrogen atom of the unsaturated ring;

in the cationic groups of formula (IV):
when x=0, then the linker arm is attached to the nitrogen atom bearing the radicals R$_8$ to R$_{10}$,
when x=1, then two of the radicals R$_8$ to R$_{10}$ form, together with the nitrogen atom to which they are attached, a saturated 5- or 6-membered ring as defined above, and the linker arm D is borne by a carbon atom of the saturated ring;

X$^-$ is chosen from monovalent and divalent anions;
it being understood that:
the number of unsaturated cationic groups Z of formula (II) or (III) is at least equal to 1;
when at least one of R$_4$, R$_5$, R'$_4$, and R'$_5$, is chosen from Z groups in which the linker arm D represents an alkyl chain comprising a ketone function, then the ketone function is not directly attached to the nitrogen atom of the group —NR$_4$R$_5$ or —NR'$_4$R'$_5$.

27. A process according to claim 26, wherein said applying step is carried out by contact with air without addition of an oxidizing agent.

28. A multi-compartment dyeing device or multi-compartment dyeing kit, comprising, a first compartment containing at least one dye composition, and a second compartment containing at least one oxidizing composition, wherein said at least one dye composition comprises at least one ingredient chosen from compounds of formula (I), below, and acid addition salts thereof:

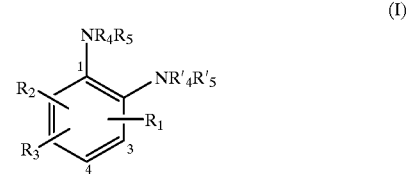

(I)

wherein:

R$^1$, R$^2$ and R$^3$, which may be identical or different, are chosen from a hydrogen atom; halogen atoms; Z groups; (C$_1$–C$_6$)alkylcarbonyls; amino(C$_1$–C$_6$) alkylcarbonyls; N—Z-amino(C$_1$–C$_6$)alkylcarbonyls; N—(C$_1$–C$_6$)alkylamino(C$_1$–C$_6$)alkylcarbonyls; N,N-di (C$_1$–C$_6$)alkylamino(C$_1$–C$_6$)alkylcarbonyls; amino (C$_1$–C$_6$)alkylcarbonyl(C$_1$–C$_6$)alkyls; N—Z-amino (C$_1$–C$_6$)alkylcarbonyl(C$_1$–C$_6$)alkyls; N—(C$_1$–C$_6$) alkylamino(C$_1$–C$_6$)alkylcarbonyl(C$_1$–C$_6$)alkyls; N,N-di(C$_1$–C$_6$)alkylamino(C$_1$–C$_6$)alkylcarbonyl(C$_1$–C$_6$) alkyls; carboxyl; (C$_1$–C$_6$)alkylcarboxyls; (C$_1$–C$_6$) alkylsulphonyls; aminosulphonyls; N—Z-aminosulphonyls; (C$_1$–C$_6$)N-alkylaminosulphonyls; N,N-di(C$_1$–C$_6$)alkylaminosulphonyls; (C$_1$–C$_6$) aminosulphonylalkyls; (C$_1$–C$_6$)N—Z-aminosulphonylalkyls; N—(C$_1$–C$_6$) alkylaminosulphonyl(C$_1$–C$_6$)alkyls; N,N-di(C$_1$–C$_6$) alkylaminosulphonyl(C$_1$–C$_6$)alkyls; carbamyl; N—(C$_1$–C$_6$)alkylcarbamyls; N,N-di(C$_1$–C$_6$) alkylcarbamyls; carbamyl(C$_1$–C$_6$)alkyls; N—(C$_1$–C$_6$) alkylcarbamyl(C$_1$–C$_6$)alkyls; N,N-di(C$_1$–C$_6$) alkylcarbamyl(C$_1$–C$_6$)alkyls; (C$_1$–C$_6$)alkyls; (C$_1$–C$_6$) monohydroxyalkyls; (C$_2$–C$_6$)polyhydroxyalkyls; (C$_1$–C$_6$)alkoxy(C$_1$–C$_6$)-alkyls; (C$_1$–C$_6$)trifluoroalkyls; cyano; OR$_6$ and SR$_6$ groups; amino groups protected with a radical chosen from (C$_1$–C$_6$)alkylcarbonyls, (C$_1$–C$_6$)alkylcarboxyls, trifluoro(C$_1$–C$_6$) alkylcarbonyls, amino(C$_1$–C$_6$)alkylcarbonyls, N—Z-amino(C$_1$–C$_6$)alkylcarbonyls, N—(C$_1$–C$_6$)alkylamino (C$_1$–C$_6$)alkylcarbonyls, N,N-di(C$_1$–C$_6$)alkylamino (C$_1$–C$_6$)alkylcarbonyls, (C$_1$–C$_6$)alkylcarboxyls, carbamyl, N—(C$_1$–C$_6$)alkylcarbamyls, N,N-di(C$_1$–C$_6$) alkylcarbamyls, (C$_1$–C$_6$)alkylsulphonyls, aminosulphonyls, N—Z-aminosulphonyls, (C$_1$–C$_6$)N-alkylaminosulphonyls, N,N-di(C$_1$–C$_6$) alkylaminosulphonyls, thiocarbamyl, formyl, and Z groups, in which the linker arm D of the Z group comprises a ketone function directly attached to the nitrogen atom of the amino group; and $(C_1-C_6)$ aminoalkyl in which the amine is substituted with at least one, identical or different radical, chosen from $(C_1-C_6)$alkyls, $(C_1-C_6)$monohydroxyalkyls, $(C_2-C_6)$ polyhydroxyalkyls, $(C_1-C_6)$alkylcarbonyls, carbamyl, N—$(C_1-C_6)$alkyl-carbamyls, N,N-di$(C_1-C_6)$ alkylcarbamyls, $(C_1-C_6)$alkylsulphonyls, formyl, trifluoro$(C_1-C_6)$alkyl-carbonyls, $(C_1-C_6)$ alkylcarboxyls, thiocarbamyl, and Z groups;

$R_6$ is a radical chosen from $(C_1-C_6)$alkyls; $(C_1-C_6)$ monohydroxyalkyls; $(C_2-C_6)$polyhydroxyalkyls; Z groups; $(C_1-C_6)$alkoxy$(C_1-C_6)$alkyls; aryls; benzyl; carboxy$(C_1-C_6)$alkyls; $(C_1-C_6)$alkylcarboxy$(C_1-C_6)$ alkyls; cyano$(C_1-C_6)$alkyls; carbamyl$(C_1-C_6)$alkyls; N—$(C_1-C_6)$alkylcarbamyl$(C_1-C_6)$alkyls; N,N-di $(C_1-C_6)$alkylcarbamyl$(C_1-C_6)$alkyls; $(C_1-C_6)$ trifluoroalkyls; $(C_1-C_6)$aminosulphonylalkyls; $(C_1-C_6)$N—Z-aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; $(C_1-C_6)$ alkylsulphinyl$(C_1-C_6)$alkyls; $(C_1-C_6)$alkylsulphonyl $(C_1-C_6)$alkyls; $(C_1-C_6)$alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$ monohydroxyalkyls, $(C_2-C_6)$polyhydroxyalkyls, $(C_1-C_6)$alkylcarbonyls, formyl, trifluoro-$(C_1-C_6)$ alkylcarbonyls, $(C_1-C_6)$alkylcarboxyls, carbamyl, N—$(C_1-C_6)$alkylcarbamyls, N,N-di-$(C_1-C_6)$ alkylcarbamyls, thiocarbamyl and $(C_1-C_6)$ alkylsulphonyls, and Z groups;

$R_4$, $R'_4$, $R_5$ and $R'_5$, which may be identical or different, are substituents chosen from a hydrogen atom; Z groups; $(C_1-C_6)$alkyls; $(C_1-C_6)$monohydroxyalkyls; $(C_2-C_6)$polyhydroxyalkyls; $(C_1-C_6)$alkoxy$(C_1-C_6)$ alkyls; aryls; benzyl; cyano$(C_1-C_6)$alkyls; carbamyl $(C_1-C_6)$alkyls; N—$(C_1-C_6)$alkylcarbamyl$(C_1-C_6)$ alkyls; N,N-di$(C_1-C_6)$alkylcarbamyl$(C_1-C_6)$alkyls; thiocarbamyl$(C_1-C_6)$alkyls; $(C_1-C_6)$trifluoroalkyls; $(C_1-C_6)$sulphoalkyls; $(C_1-C_6)$alkylcarboxy$(C_1-C_6)$ alkyls; $(C_1-C_6)$alkylsulphinyl$(C_1-C_6)$alkyls; $(C_1-C_6)$ aminosulphonylalkyls; $(C_1-C_6)$N—Z- aminosulphonylalkyls; N—$(C_1-C_6)$ alkylaminosulphonyl$(C_1-C_6)$alkyls; N,N-di$(C_1-C_6)$ alkylaminosulphonyl$(C_1-C_6)$alkyls; $(C_1-C_6)$ alkylcarbonyl$(C_1-C_6)$alkyls; $(C_1-C_6)$aminoalkyls; $(C_1-C_6)$aminoalkyls in which the amine is substituted with one or two, identical or different, radicals chosen from $(C_1-C_6)$alkyls, $(C_1-C_6)$monohydroxyalkyls, $(C_2-C_6)$polyhydroxyalkyls, $(C_1-C_6)$alkylcarbonyls, carbamyl, N—$(C_1-C_6)$alkylcarbamyls, N,N-di$(C_1-C_6)$ alkylcarbamyls, $(C_1-C_6)$alkylsulphonyls, formyl, trifluoro$(C_1-C_6)$alkylcarbonyls, $(C_1-C_6)$ alkylcarboxyls, thiocarbamyl, and Z groups;

Z is chosen from unsaturated cationic groups of formulae (II) and (III) below, and the saturated cationic groups of formula (IV) below:

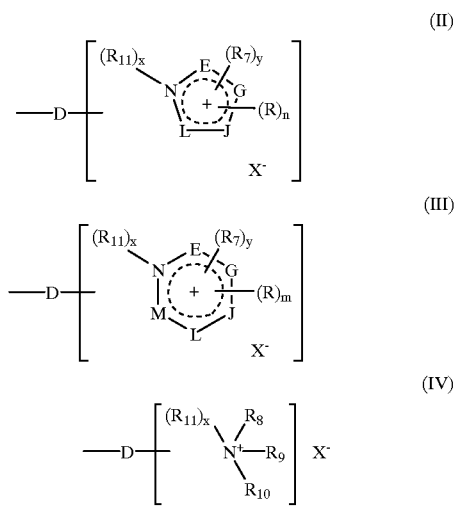

in which:

D is a linker arm chosen from linear and branched alkyl chains, optionally interrupted by at least one hetero atom, such as oxygen, sulphur, and nitrogen atoms, and optionally substituted with at least one radical chosen from a hydroxyl group and $(C_1-C_6)$alkoxys, and which can optionally bear at least one ketone function;

the ring members E, G, J, L and M, which may be identical or different, are chosen from carbon, oxygen, sulphur, and nitrogen atoms;

n is chosen from the integers 0, 1, 2, 3, and 4;

m is chosen from the integers 0, 1, 2, 3, 4, and 5;

the radicals R, which may be identical or different, are chosen from a second group Z which is identical to or different from the first group Z, a halogen atom, a hydroxyl, $(C_1-C_6)$alkyls, $(C_1-C_6)$ monohydroxyalkyls, $(C_2-C_6)$polyhydroxyalkyls, a nitro, a cyano, cyano$(C_1-C_6)$alkyls, $(C_1-C_6)$alkoxys, tri$(C_1-C_6)$alkylsilane$(C_1-C_6)$alkyls, amido, aldehydo, carboxyl, $(C_1-C_6)$alkylcarbonyls, thio, $(C_1-C_6)$thioalkyls, $(C_1-C_6)$alkylthios, amino, aminos protected with a radical chosen from $(C_1-C_6)$ alkylcarbonyls, carbamyls and $(C_1-C_6)$ alkylsulphonyls; NHR" groups, NR" R'" groups in which R" and R'", which may be identical or different, are chosen from $(C_1-C_6)$alkyl radicals, $(C_1-C_6)$monohydroxyalkyl radicals, and $(C_2-C_6)$ polyhydroxyalkyl radicals;

$R_7$ is a radical chosen from $(C_1-C_6)$alkyls, $(C_1-C_6)$ monohydroxyalkyls, $(C_2-C_6)$polyhydroxyalkyls, cyano$(C_1-C_6)$alkyls, tri$(C_1-C_6)$alkylsilane$(C_1-C_6)$ alkyls, $(C_1-C_6)$alkoxy$(C_1-C_6)$alkyls, carbamyl- $(C_1-C_6)$alkyls, $(C_1-C_6)$alkylcarboxy$(C_1-C_6)$alkyls, benzyl and a second group Z which is identical to or different from the first group Z;

$R_8$, $R_9$ and $R_{10}$, which may be identical or different, are radicals chosen from $(C_1-C_6)$alkyls, $(C_1-C_6)$ monohydroxyalkyls, $(C_2-C_6)$polyhydroxyalkyls, $(C_1-C_6)$alkoxy$(C_1-C_6)$alkyls, cyano$(C_1-C_6)$alkyls, aryls, benzyl, $(C_1-C_6)$amidoalkyls, tri$(C_1-C_6)$ alkylsilane$(C_1-C_6)$alkyls, and $(C_1-C_6)$aminoalkyls in which the amine is protected with a radical chosen from $(C_1-C_6)$alkylcarbonyls, carbamyl, and $(C_1-C_6)$ alkylsulphonyls; two of the radicals $R_8$, $R_9$ and $R_{10}$ can together also form, with the nitrogen atom to which they are attached, a saturated 5- or 6-membered ring or a ring containing at least one additional hetero atom, the ring being optionally substituted with a substituent chosen from halogen atoms, a hydroxyl group, $(C_1-C_6)$alkyls, $(C_1-C_6)$monohydroxyalkyls, $(C_2-C_6)$polyhydroxyalkyls, a nitro, a cyano, cyano$(C_1-C_6)$alkyls, $(C_1-C_6)$alkoxys, tri$(C_1-C_6)$alkylsilane$(C_1-C_6)$alkyls, amido, aldehydo, carboxyl, keto$(C_1-C_6)$alkyls, thio, $(C_1-C_6)$thioalkyls, $(C_1-C_6)$alkylthios, amino, and aminos protected with a radical chosen from $(C_1-C_6)$alkylcarbonyls, carbamyl, and $(C_1-C_6)$alkylsulphonyls; one of the radicals $R_8$, $R_9$ and $R_{10}$ can also be chosen from a second group Z which is identical to or different from the first group Z;

$R_{11}$ is a radical chosen from $(C_1-C_6)$alkyls; $(C_1-C_6)$monohydroxyalkyls; $(C_2-C_6)$polyhydroxyalkyls; aryls; benzyl; $(C_1-C_6)$aminoalkyls, $(C_1-C_6)$aminoalkyls in which the amine is protected with a radical chosen from $(C_1-C_6)$alkylcarbonyls, carbamyl, and $(C_1-C_6)$alkylsulphonyls; carboxy$(C_1-C_6)$alkyls; cyano$(C_1-C_6)$alkyls; carbamyl$(C_1-C_6)$alkyls; $(C_1-C_6)$trifluoroalkyls; tri$(C_1-C_6)$alkylsilane$(C_1-C_6)$alkyls; $(C_1-C_6)$sulphonamidoalkyls; $(C_1-C_6)$alkylcarboxy$(C_1-C_6)$alkyls; $(C_1-C_6)$alkylsulphinyl$(C_1-C_6)$alkyls; $(C_1-C_6)$alkylsulphonyl$(C_1-C_6)$alkyls $(C_1-C_6)$alkylketo$(C_1-C_6)$alkyls; N—$(C_1-C_6)$alkylcarbamyl$(C_1-C_6)$alkyls; N—$(C_1-C_6)$alkylsulphonamido$(C_1-C_6)$alkyls;

x and y are integers chosen from 0 and 1; with the provision that:
in the unsaturated cationic groups of formula (II):
when x=0, the linker arm D is attached to the nitrogen atom,
when x=1, the linker arm D is attached to one of the ring members E, G, J or L,
y can take the value 1 only:
1) when the ring members E, G, J and L simultaneously represent a carbon atom and when the radical $R_7$ is borne by the nitrogen atom of the unsaturated ring; or alternatively
2) when at least one of the ring members E, G, J and L represents a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L or M,
y can take the value 1 only when at least one of the ring members E, G, J, L and M is chosen from divalent atoms and when the radical $R_7$ is borne by the nitrogen atom of the unsaturated ring;
in the cationic groups of formula (IV):
when x=0, then the linker arm is attached to the nitrogen atom bearing the radicals $R_8$ to $R_{10}$,
when x=1, then two of the radicals $R_8$ to $R_{10}$ form, together with the nitrogen atom to which they are attached, a saturated 5- or 6-membered ring as defined above, and the linker arm D is borne by a carbon atom of the saturated ring;

$X^-$ is chosen from monovalent and divalent anions;
it being understood that:
the number of unsaturated cationic groups Z of formula (II) or (III) is at least equal to 1;
when at least one of $R_4$, $R_5$, $R'_4$, and $R'_5$, is chosen from Z groups in which the linker arm D represents an alkyl chain comprising a ketone function, then the ketone function is not directly attached to the nitrogen atom of the group —$NR_4R_5$ or —$NR'_4R'_5$.

29. A process according to claim 28, wherein said oxidizing agent is chosen from hydrogen peroxide, urea peroxide, alkali metal bromates, persalts, and enzymes.

30. A process according to claim 29, wherein said persalts are chosen from perborates and persulphates, and said enzymes are chosen from peroxidases and 2-electron oxidoreductases.

31. A process according to claim 27, wherein the coloration is developed at acidic, neutral or alkaline pH by employing an oxidizing agent which is added to the dye composition to form a mixture that is then applied to said keratin fibres, or which is present in an oxidizing composition which is applied to said keratin fibres simultaneously with said dye composition or sequentially in a separate manner from said dye composition.

* * * * *

UNITED STATES PATENT AND TRADEMARK OFFICE
CERTIFICATE OF CORRECTION

PATENT NO. : 6,340,371 B1
DATED : January 22, 2002
INVENTOR(S) : Genet et al.

It is certified that error appears in the above-identified patent and that said Letters Patent is hereby corrected as shown below:

<u>Column 18,</u>
Line 38, please change "hydroxides hydrogenosulphate" to read -- hydroxide, a hydrogenosulphate --.

Signed and Sealed this

Seventh Day of May, 2002

Attest:

Attesting Officer

JAMES E. ROGAN
Director of the United States Patent and Trademark Office